(12) United States Patent
Ernsberger

(10) Patent No.: US 7,892,071 B2
(45) Date of Patent: Feb. 22, 2011

(54) ORTHOPAEDIC COMPONENT MANUFACTURING METHOD AND EQUIPMENT

(75) Inventor: Craig N. Ernsberger, Granger, IN (US)

(73) Assignee: DePuy Products, Inc., Warsaw, IN (US)

( * ) Notice: Subject to any disclaimer, the term of this patent is extended or adjusted under 35 U.S.C. 154(b) by 208 days.

(21) Appl. No.: 11/529,888

(22) Filed: Sep. 29, 2006

(65) Prior Publication Data
US 2008/0081539 A1    Apr. 3, 2008

(51) Int. Cl.
*B24B 1/00* (2006.01)
(52) U.S. Cl. .............................. 451/37; 451/41; 451/49; 451/57; 451/59
(58) Field of Classification Search .................. 451/36, 451/37, 49, 50, 57, 59, 60, 103, 104, 113, 451/285, 287, 41
See application file for complete search history.

(56) References Cited

U.S. PATENT DOCUMENTS

| | | | |
|---|---|---|---|
| 4,790,851 A * | 12/1988 | Suire et al. .................. 128/898 |
| 5,449,313 A | 9/1995 | Kordonsky et al. |
| 5,788,558 A * | 8/1998 | Klein ........................... 451/36 |
| 6,077,148 A * | 6/2000 | Klein et al. .................... 451/11 |
| 6,332,829 B1 | 12/2001 | Trommer |
| 6,402,978 B1 | 6/2002 | Levin |
| 6,413,441 B1 | 7/2002 | Levin |
| 6,503,414 B1 | 1/2003 | Kordonsky et al. |
| 6,561,874 B1 | 5/2003 | Kordonski |
| 6,719,611 B2 | 4/2004 | Kordonski et al. |
| 6,746,310 B2 | 6/2004 | Tricard et al. |
| 6,776,688 B2 | 8/2004 | Kim et al. |
| 2003/0013386 A1* | 1/2003 | Weinstein et al. ............. 451/41 |
| 2003/0087585 A1 | 5/2003 | Kordonsky et al. |
| 2003/0110706 A1 | 6/2003 | Rosenflanz |
| 2004/0192171 A1 | 9/2004 | Koike |
| 2004/0229553 A1 | 11/2004 | Bechtold et al. |
| 2004/0266319 A1 | 12/2004 | Kordonski et al. |
| 2005/0054276 A1 | 3/2005 | Shamshidov et al. |
| 2005/0076579 A1* | 4/2005 | Siddiqui et al. ............... 51/307 |
| 2005/0079812 A1 | 4/2005 | Bechtold |
| 2005/0263171 A1 | 12/2005 | Wu et al. |

FOREIGN PATENT DOCUMENTS

WO    02086180    10/2002

OTHER PUBLICATIONS

M.R. Oliver, *Chemical-Mechanical Planarization of Semiconductor Material*, Springer-Verlag Berlin Heidelberg (2004).

(Continued)

*Primary Examiner*—Eileen P. Morgan
(74) *Attorney, Agent, or Firm*—Maginot, Moore & Beck

(57) ABSTRACT

A method of reducing the surface roughness of articulating surfaces of orthopaedic implants is provided. The method includes the steps of providing an abrasive particle providing a chemical including at least one of an oxidant, a corrosion inhibitor, a complexing agent and a surfactant, combining the chemical with the abrasive particle to form a slurry, and polishing the implant with the slurry.

20 Claims, 21 Drawing Sheets

OTHER PUBLICATIONS

Chan et al., "The Otto Aufranc Award - Wear and Lubrication of Metal-on-Metal Hip Implants," Clinical Orthopaedics and Related Research, 1999, pp. 10-24, No. 369, Lippincott Williams & Wilkins, Inc., USA (15 pages).

Hamrock, "Fundamentals of Fluid Film Lubrication, Figure 1-8 and Figure 1-9," Nasa Reference Publication 1255, Aug. 1991, The Ohio State University, Columbus, USA (5 pages).

Johnson et al., "A Simple Theory of Asperity Contact in Elastohydro-Dynamic Lubrication," Wear, Paper presented at Conference on "The Limits of Lubrication", Jul. 1971, pp. 91-108, Elsevier Sequoia S.A., Lausanne, printed in the Netherlands (18 pages).

Tricard et al., "Sub-Aperture Approaches for Asphere Polishing and Metrology," Invited Paper, QED Technologies, Inc., Proceedings of SPIE, pp. 284-299, vol. 5638, Bellingham, WA (16 pages).

Walker et al., "The 'Precessions' tooling for polishing and figuring flat, spherical and aspheric surfaces," Optics Express, Apr. 21, 2003, pp. 958-964, vol. 11, No. 8, Optical Society of America, USA (7 pages).

* cited by examiner

ORTHOPAEDIC COMPONENT MANUFACTURING METHOD AND EQUIPMENT

TECHNICAL FIELD OF THE INVENTION

The present invention relates generally to the field of orthopaedics, and more particularly, to an implant for use in arthroplasty.

BACKGROUND OF THE INVENTION

The skeletal system includes many long bones that extend from the human torso. These long bones include the femur, fibula, tibia, humerus, radius and ulna.

A joint within the human body forms a juncture between two or more bones or other skeletal parts. The ankle, hip, knee, shoulder, elbow and wrist are just a few examples of the multitude of joints found within the body. As should be apparent from the above list of examples of joints, many of the joints permit relative motion between the bones. For example, the motion of sliding, gliding, and hinge or ball and socket movements may be had by a joint. For example, the ankle permits a hinge movement, the knee allows for a combination of gliding and hinge movements and the shoulder and hip permit movement through a ball and socket arrangement.

The joints in the body are stressed or can be damaged in a variety of ways. For example, gradual wear and tear is imposed on the joints through the continuous use of a joint over the years. The joints that permit motion have cartilage positioned between the bones providing lubrication to the motion and also absorbing some of the forces direct to the joint. Over time, the normal use of a joint may wear down the cartilage and bring the moving bones in a direct contact with each other. In contrast, in normal use, a trauma to a joint, such as the delivery of a large force, from an accident, for example, an automobile accident, may cause considerable damage to the bones, the cartilage or to other connective tissue such as tendons or ligaments.

Arthropathy, a term referring to a disease of the joint, is another way in which a joint may become damaged. Perhaps the best known joint disease is arthritis, which is generally referred to a disease or inflammation of a joint that results in pain, swelling, stiffness, instability, and often deformity.

There are many different forms of arthritis, with osteoarthritis being the most common and resulting from the wear and tear of a cartilage within a joint. Another type of arthritis is osteonecrosis, which is caused by the death of a part of the bone due to loss of blood supply. Other types of arthritis are caused by trauma to the joint while others, such as rheumatoid arthritis, Lupus, and psoriatic arthritis destroy cartilage and are associated with the inflammation of the joint lining.

The hip joint is one of the joints that is commonly afflicted with arthropathy. The hip joint is a ball and socket joint that joins the femur or thighbone with the pelvis. The pelvis has a semispherical socket called the acetabulum for receiving a ball socket head in the femur. Both the head of the femur and the acetabulum are coated with cartilage for allowing the femur to move easily within the pelvis. Other joints commonly afflicted with arthropathy include the spine, knee, shoulder, carpals, metacarpals, and phalanges of the hand.

Arthroplasty as opposed to arthropathy commonly refers to the making of an artificial joint. In severe cases of arthritis or other forms of arthropathy, such as when pain is overwhelming or when a joint has a limited range of mobility, a partial or total replacement of the joint within an artificial joint may be justified. The procedure for replacing the joint varies, of course, with the particular joint in question, but in general involves replacing a terminal portion of an afflicted bone with a prosthetic implant and inserting a member to serve as a substitute for the cartilage.

The prosthetic implant is formed of a rigid material that becomes bonded with the bone and provides strength and rigidity to the joint and the cartilage substitute members chosen to provide lubrication to the joint and to absorb some of the compressive forces. Suitable materials for the implant include metals and composite materials such as titanium, cobalt chromium, stainless steel, ceramic and suitable materials for cartilage substitutes include polyethylene, ceramics, and metals. A cement may also be used to secure the prosthetic implant to the host bone.

A total hip replacement, for example, involves removing the ball shaped head of the femur and inserting a stem implant into the center of the bone, which is referred to as the medullary canal, or marrow of the bone. The stem implant may be cemented into the medullary canal or may have a porous coated surface for allowing the bone to heal directly to the implant. The stem implant has a neck and a ball shaped head, which are intended to perform the same functions as a healthy femur's neck and a ball shaped head. The polyethylene cup is inserted into the acetabulum and has a socket for receiving the head on the stem implant.

The polyethylene cup may be positioned directly into the acetabulum. Preferably, the polyethylene cup is secured to a metal member, which is in turn secured to the acetabulum. This metal member is typically called a cup or a shell. The cup or shell may include a porous coating for promoting bony in-growth to secure the shell to the acetabulum. Alternatively or in addition the shell may include an opening or a plurality of openings for receiving bone screws to assist in the attachment of the shell to the acetabulum. As an alternative to the polyethylene cup, a cup of a different material may be inserted into the shell. For example, the cup may be made of a metal, for example, cobalt chromium, stainless steel, or titanium. Alternatively, the cup may be made of a ceramic.

More recently, the polyethylene cup as a hip cup prosthesis has been replaced with a more rigid component. For example, in more recent hip cup prostheses, the cup is made of, for example, a metal or a ceramic. The head may be made of a metal or a ceramic. For example, the cup may be made of a ceramic and the head may likewise be made of a ceramic. Alternatively, the cup may be made of a metal and the head may likewise be made of that similar metal. It should be appreciated that a ceramic cup may be utilized with a metal head and a metal cup may be utilized with a ceramic head.

Metal on Metal (MoM) hip joint prosthesis achieve very low wear rates. Steady state wear rates are negligible. The vast majority of wear debris generation occurs during the so called break-in phase. During this phase, the metal surfaces are thought to "run-in" producing a highly conformal joint that is efficiently lubricated by synovial fluid components. It would be of great benefit to eliminate this break-in wear period.

Wear rates of articulating surfaces are in large part determined by the lubrication regime that may be established between the two surfaces. Three lubrication regimes are often described in the literature: Partial or Boundary, Elastohydrodynamic, and full Hydrodynamic. The friction and wear behavior characteristic of these lubrication regimes is illustrated in FIGS. 22 and 23, respectively, taken from "Fundamentals of Fluid Film Lubrication" by Bernard Hamrock (NASA publication 1255, dated 1991).

To maximize the life of the prosthesis, the accuracy of the dimensional characteristics of the components of the prosthesis as well as the surface condition, for example the surface finish, is extremely critical in the life of the prosthesis. Dimensional errors and surface finish imperfections may cause the prosthesis to prematurely wear. The components that wear on the prosthesis, particularly those that wear rapidly, may lead to reactions with the tissues of the body. Such reaction to foreign objects is called osteolysis. Osteolysis can damage soft tissue and further complicate the replacement of the prosthesis.

Attempts have been made to provide for improved finishes and geometries of the articulating surface of a prosthesis. For example, the surfaces may be polished by hand by, for example, a rubbing compound or by a metal or cloth buffing wheel. Alternatively, the surfaces may be smoothed by robotic manipulators using similar tools as are used by hand. Alternatively, the components have the articulating surface of the prosthesis may be polished by a finishing device, for example a RotoFinish® tumbling machine. These prior art attempts at providing improved geometry and finish to the articulating surface of a prosthetic component are slow and inaccurate. Further, attempts to improve the finish on the part may affect its geometry or shape. Imperfections in shape and or finish may greatly reduce the operating life of the prosthesis and may lead to osteolysis.

Processes have been developed for improving surfaces of optical components. For example a Magnetorheological Polishing fluid (hereinafter referred to as "MP-fluid") may be used in a computer controlled machine to polish optical components. The fluids are mixtures of abrasive particles and magnetic particles. The abrasive particles are in suspension and magnetic particles are in suspension in a fluid. The magnetic particles are coated with Teflon®, a trademark of E.I. DuPont de Nemours and Company, to protect them from degradation. These particles could be suspended in solutions of glycerin, glycol, water, oil, alcohol, or mixtures thereof. When a magnetic field is applied, the magnetic particles create a plastic zone, and the abrasive particle provide for polishing action. The fluids are used in manufacturing equipment that utilizes the MP-fluid finishing process is commercially available from QED Technology, Inc., Rochester, N.Y. and sold as the Q-22MRF System.

Another process has been developed by University College, London WC1E6BT, England and Zeeko Ltd., Precise Group, The Stables, East Lockinge, Oxfordshire, OX12 8QJ, England. These efforts are more fully described in an article entitled "The 'Precessions" Tooling for Polishing and Figuring Flat, spherical and Aspheric Surfaces" published in the Apr. 21, 2003 Optics Express, Vol. 11, No. 8, hereby incorporated herein in its entirety by reference.

The process is known as the Precessions™ process. Machines incorporating the Precessions process may be acquired from Satisloh North America Inc., N116W18111 Morse Drive, Germantown, Wis. 53022 USA. Machines are available from Zeeko Ltd, The Stables, East Lockinge, Wantage, Oxfordshire, OX12 8QJ, United Kingdom.

The baseline of the Precessions process is a physical subdiameter tool operating in the presence of a polishing slurry, The tooling is hosted by a 7-axis CNC polishing machine available from Satisloh North America Inc. The tool comprises an inflated, bulged rubber membrane of spherical form, covered with one of the usual proprietary non-pitch flexible polishing surfaces familiar to opticians. The tool is rotated. The rotation axis of the tool is inclined to the surface to be polished at an angle of typically 10 to 25 degrees.

Partial or boundary lubrication is characterized by extremely thin lubrication films and considerable metal to metal contact. At the other end of the spectrum, in hydrodynamic lubrication, the load is fully supported by a layer of lubricant that prevents the surfaces from contacting. Wear rates are negligible in this latter regime. Lubrication fluid film thickness is proportional to velocity and inversely proportional to load. Full hydrodynamic lubrication is considered to be achieved when the ratio of film thickness to surface roughness exceeds a value of about 3. (Johnson K L, Greenwood J A, Poon S Y: A simple theory of asperity contact in elastohydrodynamic lubrication. Wear 19:91-108, 1972), incorporated herein in its entireties by reference.

This ratio is defined as lamda=$\lambda$=H/Rq where Rq=$(Rq_a^2+Rq_b^2)^{1/2}$ where $Rq_a$ and $Rq_b$ are the rms surface roughness of the two articulating surfaces. This equation shows that smoother surfaces will achieve full hydrodynamic lubrication at lower velocities and higher loads than rougher surfaces. For example, if two surfaces have a $\lambda$=1 with Rq's of 0.01 um, we can achieve a $\lambda$ of 10 by reducing the rms surface roughness to 0.001 um.

The rougher surface would be operating in a clear boundary layer lubrication regime while the smoother surface would be completely in the hydrodynamic regime at the same speed and load. This benefit has generally been appreciated in the orthopaedic industry and considerable attention is paid to maintaining low errors of form and low surface roughness in articulating metal on metal hip components. The subject has been documented particularly well by Chan (F. W. Chan, D. Bobyn, J. B. Medley, J. J. Krygier, M Tanzer, "Wear and lubrication of metal on metal hip implants" Clinical Orthopaedics and related research number 369, pp 10-24, 1991)), incorporated herein in its entireties by reference.

FIG. 2, taken from this reference shows the experimental results they obtained on the wear of metal on metal hip implants in a hip wear simulator. From the data presented in this paper, one can predict a 53% reduction in wear of Metal on Metal Hip implants if Ra surface roughness can be reduced from present industry values of about 10 nm to 2 nm.

On the other hand, little progress has been made in reducing surface finish values below 10 nm in a production environment. Finishing procedures generally consist of polishing the finished femoral and acetabular components with a fabric impregnated with fine abrasive materials that remove material by strictly mechanical means. The polishing process causes some plastic working of the surface as metal is removed. A mechanically polished surface yields an abundance of scratches, strains, metal debris and embedded abrasives, and always distorts the metal surface. Burnishing metal by lapping or buffing decreases the rms roughness of a surface, but it never completely removes the debris and damaged metal caused by mechanical polishing.

Additionally, the microstructure of typical CoCrMoC alloys used in orthopaedics is generally two phase consisting of the matrix plus metal carbides. The later are significantly harder than the matrix. The result is that mechanical polishing generally leaves the harder carbide phases sticking out somewhat from the metal matrix. This contributes to a higher rms surface roughness than otherwise could be obtained.

The present invention is adapted to solve at least some of the aforementioned problems with the prior art.

SUMMARY OF THE INVENTION

This invention is directed to methods and apparatuses to lower surface finishes on articulating surfaces of orthopaedic implant components. More particularly, this invention is directed to a highly accurate method of preparing implant components using Chemical Mechanical Polishing (CMP).

Both of the issues raised above can be addressed if a chemical component is added to the polishing process. This approach has been taken by the semiconductor industry to planarize and polish patterned silicon wafers. The process was originally referred to as Chemical Mechanical Planarization (CMP) and is more often now referred to as Chemical Mechanical Polishing. Since the semiconductor wafer CMP process is reasonably mature, it will be described in some detail to illustrate the basic aspects of the process. A thorough discussion of the subject may be found in "Chemical-Mechanical Planarization of Semiconductor Materials edited by M.R. Oliver and published by Springer.

The CMP process is similar to mechanical polishing processes in that the object to be polished is brought into contact with an abrasive slurry carried by a polishing pad in relative motion to the object. In addition to the abrasive, certain chemicals are added to the slurry that dramatically effect material removal rates and the surface roughness of the object. The exact mechanisms that contribute to the low surface roughness and high removal rates are still a matter of some debate. Certain generalities can be cited but it is understood that these mechanistic explanations in no way limit the application of the CMP process to orthopaedic implants. Chemical additives may be categorized as follows.

In general, it is thought to be advantageous to produce a relatively soft or non-adherent film on the surface to be CMP'd. The action of the abrasive then removes this layer without damaging the underlying material. The chemistry of the slurry is adjusted such that the film is replenished continuously during the polishing process. In some cases, this can be obtained simply by control of pH. For example, in the case of polishing Silicon Dioxide, highly polished and planer surfaces are achieved by adjusting the pH to values of about 11. It is believed that at this pH, the surface of the oxide is hydroxylated and that this material is efficiently removed by the abrasive without damaging the underlying oxide layer. In general, it is thought that one wants to operate in the passive regime defined by the Pourbaix diagram of the material to be polished. In the Pourbaix diagram, one plots electrode potential vs pH and finds that there are certain regions in which corrosion of the material will take place and regions in which a passive, self limiting film forms. The latter region is the one that is desired in CMP, although there are clear exceptions.

The article "Chemical-Mechanical Planarization of Semiconductor Materials" edited by M.R. Oliver and published by Springer is hereby incorporated by reference in its entireties.

According to an aspect of the present invention, a method of reducing the surface roughness of articulating surfaces of orthopaedic implants is provided. The method includes the steps of providing an abrasive particle providing a chemical including at least one of an oxidant, a corrosion inhibitor, a complexing agent and a surfactant, combining the chemical with the abrasive particle to form a slurry, and polishing the implant with the slurry.

According to another aspect of the present invention an orthopaedic implant with an articulating surface polished by a method is provided. The method includes the steps of providing an abrasive particle, providing a chemical including at least one of an oxidant, a corrosion inhibitor, a complexing agent and a surfactant, combining the chemical with the abrasive particle to form a slurry, and polishing the implant with the slurry.

In another aspect, the present invention provides a system for use in preparing an articulating surface of a metal component of an orthopaedic implant. The system includes a slurry having an abrasive particle and a chemical having at least one of an oxidant, a corrosion inhibitor, a complexing agent and a surfactant. The system includes a device having a frame and a vessel for containing the slurry in a polishing zone. The device also has a mechanism for securing the component and for creating relative motion between the slurry and the surface of the component. The device and the vessel are operatively connected to the frame.

In another aspect of the system of the present invention, the vessel for containing said slurry comprises a pad.

In another aspect of the system of the present invention, the device further includes a pressure plate for applying a force on the implant and against the pad. The slurry is positioned between the implant and the pad.

In another aspect, the present invention provides a device for use with a slurry in preparing an articulating surface of a metal component of an orthopaedic implant. The device includes a frame and a vessel for containing the slurry in a polishing zone. The device includes a mechanism for securing the component and for creating relative motion between the slurry and the surface of the component. The mechanism and the vessel are operatively connected to the frame.

In another aspect of the device of the present invention, the device further includes a controller for determining the rate of material removal from the component, for determining the direction and velocity of movement of the polishing zone relative to the component and for determining the number of cycles of polishing required.

In another aspect of the device of the present invention, the device further includes a controller for determining the rate of material removal from the component, for determining the direction and velocity of movement of the polishing zone relative to the component and for determining the number of cycles of polishing required.

In another aspect of the device of the present invention, the abrasive particle of said slurry comprises a metal oxide.

In another aspect of the device of the present invention, the vessel for containing the slurry includes a pad.

In another aspect of the device of the present invention, the device further includes a pressure plate for applying a force on the implant and against the pad, with the slurry being between the implant and the pad.

In another aspect of the device of the present invention, the device further includes a surface finish-measuring device. The surface finish measuring device is operatively connected to the controller to provide a signal to the controller indicative of the surface finish of the articulating surface of the metal component.

In another aspect of the device of the present invention, the surface finish measuring device uses optics to measure the surface finish of the articulating surface of the metal component.

In another aspect of the device of the present invention, the surface finish measuring device uses electrical conductivity to measure the surface finish of the articulating surface of the metal component.

In another aspect of the device of the present invention, the device further includes a metal particle-measuring device. The metal particle measuring device measures the content of metal particles in the slurry.

In another aspect of the device of the present invention, the metal particle measuring device includes a light emitting device for emitting light onto the slurry.

In another aspect of the device of the present invention, the metal particle measuring device further includes a meter for measuring the light reflected from the slurry.

In another aspect of the device of the present invention, the metal particle measuring device measures at least one of the turbidity, the absorption and the reflectance of the slurry.

In another aspect of the device of the present invention, the metal particle measuring device measures the electrical conductivity of the slurry.

In another aspect, the present invention provides a fixture for securing an orthopaedic implant to a machine while applying chemical mechanical polishing to an articulating surface of the implant. The fixture includes a body and means to secure the body to the machine. The fixture also includes means to secure the implant to the body.

In another aspect of the fixture of the present invention, the means to secure the implant to the body includes one of a collet, a clamp or a diaphragm.

The technical advantages of the present invention include the ability to provide a smoother area surface finish to orthopedic articulating surfaces and in particular to metal on metal articulating surfaces to reduce break-in wear and provide longer orthopedic implant life. For example, according to one aspect of the present invention a method of reducing the surface roughness of articulating surfaces on orthopedic implants is provided. The method includes the steps of providing an abrasive particle, providing a chemical including at least one of an oxidant, a corrosion inhibitor, and a complexing agent and a surfactant, combining the chemical with the abrasive particle to form a slurry and polishing the implant with a slurry. The method may also include positioning the orthopedic implant while polishing the implant with the slurry.

Thus the present invention provides for a smoother average surface finish on orthopedic implant surfaces and in particular metal on metal articulating surfaces to reduce break-in wear and to provide longer orthopedic implant life.

The technical advantages of the present invention further include the ability to provide for fewer peaks and more valleys in the surface finish on ($-R_{SK}$) to orthopedic articulating surfaces and in particular to metal to metal articulating surfaces to reduce break-in wear and to provide longer orthopedic implant life. For example, according to another aspect of the present invention, a method of reducing the surface roughness of articulating surfaces of orthopedic implants provides the step of providing an abrasive particle, providing a chemical including at least one of an oxidant, a corrosion inhibitor, and a complexing agent and a surfactant, combining the chemical with the abrasive to form a slurry and manipulating the implant while polishing the implant with the slurry.

Thus the present invention provides for a surface with fewer peaks and more valleys in the surface finish of orthopedic articulating surfaces and in particular metal on metal articulating surfaces to reduce break-in wear and provide longer orthopedic implant life.

The technical advantages of the present invention also include the ability to provide quicker polish times and less labor to polish an articulating surface of an orthopedic implant. For example, according to another aspect of the present invention a method of reducing the surface roughness of articulating surfaces of orthopedic implants is provided. The method includes a first step of providing an abrasive particle. A second step of providing a chemical including at least one of an oxidant, a corrosion inhibitor, a complexing agent and a surfactant. A third step of combing the chemical with the abrasive particle to form a slurry. A fourth step of providing an articulating device to articulate the implant and a fifth step of polishing the implant while articulating the implant and polishing the implant with the slurry.

Thus the present invention provides for quicker polish times and less labor to polish an articulating surface of an orthopedic implant.

The technical advantages of the present invention also include the ability to provide a better conformance to surface geometries for orthopedic articulating surfaces and in particular, metal on metal articulating surfaces to reduce break-in wear and provide longer orthopedic implant life. For example, according to another aspect of the present invention a method of reducing the surface roughness and to improve surface geometries of articulating surfaces of orthopedic implants includes the steps of providing an abrasive particle, providing a chemical including one of an oxidant, a corrosion inhibitor, a complexing agent and a surfactant. A third step of mixing the abrasive particle with the chemical to form a slurry, a fourth step of providing a manipulator to provide the implant in a plurality of orientations and a fifth step of polishing the implant with the slurry with the manipulator positioning the implant in a variety of positions. Thus the present invention provides for quicker polish times and less labor to polish and articulating surface of an orthopedic implant.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

Corresponding reference characters indicate corresponding parts throughout the several views. Like reference characters tend to indicate like parts throughout the several views.

DETAILED DESCRIPTION OF THE PREFERRED EMBODIMENTS

Figure 1:
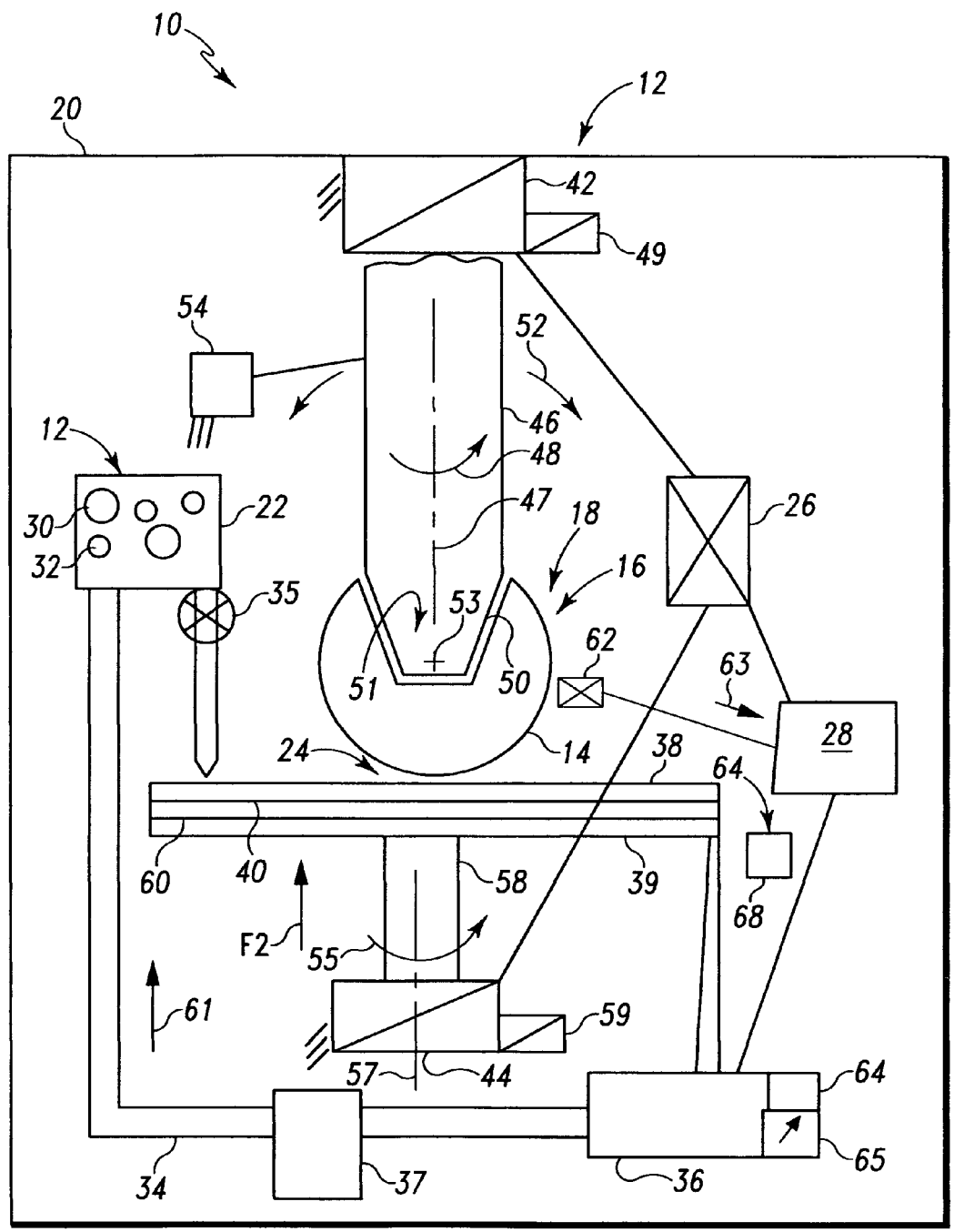
FIG. 1 is a schematic drawing of a polishing device for use to polish an orthopaedic hip head in accordance with an embodiment of the present invention.

Embodiments of the present invention and the advantages thereof are best understood by referring to the following descriptions and drawings, wherein like numerals are used for like and corresponding parts of the drawings.

In CMP of metals, it is generally found necessary to add an oxidizer. This is equivalent to increasing the electrode potential. By proper selection of pH and oxidizer, the metal removal rates and surface finish may be optimized.

Other chemical modifiers that may be added to the abrasive slurry include buffers, surfactants, complexing agents and inhibitors. Buffering reagents help maintain a constant pH during the CMP process. Complexing agents tie up or sequester material removed in the CMP process. This has the effect of changing the equilibrium concentration and can increase removal rates. Surfactants change the surface tension between the abrasive and the surrounding solution and increase the wetting of the slurry to the polished object. Finally, inhibitors selectively adsorb on a particular phase and may prevent that phase from chemical interaction with the slurry. This may allow the chemistry to be adjusted to passivate or dissolve one phase without the other phase corroding. This is especially advantageous in the etching of multiphase microstructures.

An example of the various components and their role that have been found to be useful in the CMP of Tungsten in semiconductor applications is found in table 1 below.

TABLE 1

| CMP Component | Role |
| --- | --- |
| Potassium Ferrocyanide | Oxidizer |
| Alumina or ceria | Abrasive |
| Polyoxyethylene alcohol | Surfactant |
| Ethylene Diamine | Complexing agent |
| Potassium dihydrogen Phosphate | Buffer |

Turning now to the issue of reducing surface roughness of orthopaedic implants, we recall that there are two contributions to the roughness. The first is due to aspects of the mechanical abrasive material removal process. Since the implant material has finite ductility, there will be some plastic deformation that occurs during the mechanical polishing process. This will result in local plowing of abrasive particles, scratching and smearing of the surface, and increase in associated topography. There will also inevitably be abrasive that is embedded in the surface, increasing surface roughness.

The second contribution to residual surface roughness is the multiphase microstructure of the alloy. The CoCrMoC alloys typically used in orthopaedic implants contain at least two phases. The matrix or parent phase is an FCC solid solution of Co, Cr, and Mo. Complex carbides of these elements make up the second phase, the volume fraction and distribution of which depend on Carbon content, degree of cold work, and heat treat history. These carbides differ significantly in physical and chemical properties from the matrix. With mechanical polishing, the matrix is preferentially removed and the carbide phase protrudes from the surface, increasing surface roughness.

Both contributions can be reduced by adding a chemical component to the polishing process. By removing material through chemical dissolution, the amount of cold work and plastic deformation of the part is reduced. In addition, proper selection of chemistry can allow preferential removal of one phase. In the present case, it would be advantageous to remove the carbide phase at the same or faster rate than the matrix. Alternatively, a two step process can be employed where the carbide is removed to slightly below the surface of the matrix and then the matrix is polished back to this level. This would reduce or eliminate the tendency of the harder phase to stand in relief due to faster mechanical removal rates of the parent phase.

While the process described has similar characteristics to the CMP process used in the semiconductor industry, it is novel in two regards. First, CMP is currently done only on flat surfaces. To the author's knowledge, no one has commercially applied the process to 3 dimensional articles such as orthopaedic implants. To accomplish this, special manipulators are required to expose the implant surfaces to the CMP pad.

The second novel aspect has to do with the slurry chemistry. In certain embodiments of the invention, the chemistry is adjusted such that the carbide phase is removed at equal or higher rates than the matrix phase. This allows a final surface finish in which the matrix and carbide phases are co-planer, minimizing any contribution to surface roughness. There are two separate strategies for accomplishing this.

In the first strategy, a material is added to the slurry that preferentially adsorbs on the matrix phase and prevents its dissolution by a second chemical that dissolves the carbide phase. Known corrosion inhibitors for Cobalt include Triazole compounds, Thiadiazoles (eg. Disodium 2-5 dimercapto 1-3-4 thiadzole), Alkanol amine, and other materials known to those skilled in the art of corrosion inhibition. The carbide phase can then be attacked by a combination of chemical dissolution and abrasive removal by oxidizing acids such as HNO3.

In the second strategy, a chemical is added to the slurry that preferentially dissolves the carbide phase. For example, table 2 below shows the relative etch rates of various simple and complex carbides compared to Co or Ni by "Murakami's reagent", a solution of potassium ferrocyanide in sodium hydroxide and water. Other selective etchants will be known to those skilled in the art of metallography.

TABLE 2

| Component | Reaction rate (WC = 1) | Etching duration, s |
|---|---|---|
| Co, Ni | 0 | ... |
| WC | 1 | 120 |
| (Ta,Ti,Nb,W)C | 4 | 60 |
| η phase (Co$_3$W$_3$)C | 20 | 3 |
| η phase (Co$_6$W$_6$)C | 40 | 3 |

According to the present invention and referring now to FIG. 1, a device 10 for use with a slurry 12 in preparing an articulating surface 14 of a component of an orthopaedic implant 18 is provided. The device includes a frame 20 and a vessel 22 for containing the slurry 12 in a polishing zone 24. The device 10 further includes a mechanism 26 for securing the component 16 and for creating relative motion between the slurry 12 and the articulating surface 14 of the component 16. The mechanism 26 and the vessel 22 are operatively connected to the frame 20.

As shown in FIG. 1, the device 10 may further include a controller 28 for controlling the mechanism 26 that creates relative motion between the slurry 12 and the surface 14 of the component. The controller 28 may further control the rate of removal of the material from the component 16 and may be used to determine the direction and velocity of movement of the polishing zone 24 relative to the component 16. The controller 28 may further be utilized for determining the number of cycles of polishing required.

As shown in FIG. 1, the slurry 12 may include a chemical 30 which is mixed with abrasive particles 32. The chemical may include an oxidant, a corrosion inhibitor, a complexing agent and a surfactant. The chemical may include a chemical with an oxidant capable of oxidizing one of the metals or phases in the object to be polished to a higher oxidation state than it exists in the bulk alloy. The chemical may also include a chemical with a corrosion inhibitor capable of preventing corrosion of one of the phases of the alloy in the presence of the slurry components designed to corrode or dissolve the other alloy constituents.

The chemical may also include a chemical with a complexing agent capable of sequestering components removed from the object to be polished. The chemical may also include a chemical with a surfactant capable of lowering the surface tension between the slurry abrasive component and the slurry liquid component, or lowering the surface tension between the object to be polished and the slurry liquid component.

The abrasive particle 32 may, for example, be in the form of a metal oxide. Such typical metal oxides include aluminum oxide and silicone dioxide. The abrasive particle may be dispersed in an aqueous solution including the chemical 30. The aqueous solution may be in the form of a slurry, in the form of a suspension, or in the form of a true colloid. The slurry 12 may be replaced by a polishing solution containing only the chemical 30. It should be appreciated that in such situations, the abrasive particle 32 may be incorporated into, for example, a pad material which contacts the articulating surface 14 to be polished.

The vessel 22 may have any suitable form capable of containing the slurry 12. The vessel 22 may be positioned under the articulating surface 14 of the component 16 to provide for the polishing zone 24 to be positioned within the slurry 12 in the vessel 22. The vessel 22 may, as shown in FIG. 1, be connected to a slurry circulation system 34 which circulates the slurry 12 such that the slurry 12 may separate the metal removed from the articulating surface and maintain the slurry 12 full with fresh chemicals and proper abrasive materials.

The circulating system 34 may include a pump 35 for assuring the proper flow of slurry 12 into the polishing zone 24. The circulating system 34 may further include a filtration system 36 for providing slurry in the proper condition for delivery to the polishing zone 24. The circulating system 34 may further include a heat exchanger 37 for maintaining accurate temperatures for the slurry 12. Maintaining accurate temperatures for the slurry provide for optimum temperature for the chemical reactions occurring in the slurry and to maintain size and dimensional mechanical properties of the component 16.

To assure that the slurry in the polishing zone 24 provides its removal of material from the metal component 16, the device 10 may include a polishing pad 38 to provide an area between the articulating surface and the polishing zone 24 for the slurry 12 to perform its abrasive action on the metal component 16. The polishing pad 38 may be supported by for example, a table 39. The table 39 may be made of a suitable durable material to provide a rigid support for the polishing pad 38.

Alternatively the polishing pad 38 may be supported by an inflatable diaphragm or bonnet such as that provided by Zeeko and Satisloh North America Inc. The pad 38 may be attached to an inflatable support capable of varying at least one of the polishing pressure or contact area.

The polishing pad 38 must have sufficient mechanical integrity and chemical resistance to survive the rigors of polishing. The mechanical properties of a polishing pad include high strength to resist tearing during polishing, acceptable levels of hardness and a modulus selected based on the materials being polished. The polishing pad should have good abrasion resistance to prevent excessive pad wear during polishing.

Chemically, the pad 38 must be able to survive the aggressive slurry chemistries of the chemicals 30 in the slurry 12. Slurry chemistries may include highly acidic oxidizing slurries for polishing metals. Such slurries may have a pH of less than 2 and contain oxidizing agents such as hydrogen peroxide, ferric nitrate, or potassium iodate.

The pad 38 may be supported by a plate 60. The plate 60 may also need to be sufficiently hydrophilic. If the liquid is not wet but instead beads on the polishing pad surface it will be swept away by the metal component 16 and starved of the necessary chemistry to enable effective polishing. One material which may be used in the polishing pad is polyurethane. The polishing pad 38 may include apertures 40 for trapping or receiving abrasive particles 32.

The mechanism 26 may, as shown in FIG. 1, include a work piece mechanism 42 for positioning the work piece or metal component 16 and a table mechanism 44 for positioning the table 39 with respect to the metal component 16.

The work piece mechanism 42 may, as is shown in FIG. 1, include a work piece spindle 46 which rotates about rotational axis 47 in the direction of rotational arrow 48. The work piece mechanism 42 further includes a motor 49 for rotating the work piece spindle 46. The work piece mechanism 42 further includes a fixture 50 attached to the work piece spindle 46. The fixture 50 is utilized to secure the metal component 16. As shown in FIG. 1, the fixture 50 may be in the form of a male taper to fit on internal taper 51 of the hip head or component 16.

To provide for the entire articulating surface 14 of the metal component 16 to enter into polishing zone 24 and contact the polishing pad 38, as shown in FIG. 1, the work piece spindle 46 articulates in the direction of articulation arrow 52 about pivot point 53. The pivot point 53, as shown in FIG. 1, is coincident with the center of the hip head 16 such that the hip head 16 may have the entire articulating surface 14 polished. The articulation about the pivot point 53 of the work piece mechanism 42 may be incorporated by synchronous or servo motor 54 operably connected to the work piece mechanism 42.

The table 39 may be fixedly secured to table mechanism 44 and the entire relative motion of the metal component 16 with respect to the polishing pad 38 may be accomplished by work piece mechanism 42. Alternatively, and as shown in FIG. 1, the table mechanism 44 may serve to rotate table 39 in the direction of the arrow 55. The table mechanism 44 may include a table spindle 58 which is rotated in the direction of arrow 55 by table motor 59.

The device 10 may further include a pressure plate, or platen 60, applying a force against the polishing pad 38 and eventually on the component 16. The slurry 12 will be positioned between the component 16 and the polishing pad 38. The pressure plate, or platen 60, is urged in direction of arrow 61 with a force F2 to apply an appropriate force of the polishing pad 38 against the articulating surface 14 of the component 16. The force F2 applied by the pressure plate 60 is empirically optimized to provide for the optimum metal removal and operating conditions for the device 10.

The device 10 may further include a surface finishing measuring device 62. The surface finishing measuring device 62 may be connected to the controller 28 to provide a signal 63 to the controller 28 indicative of the surface finish of the articulating surface 14 of the metal component 16.

The surface finishing measuring device 62 may utilize optics to measure the surface finish of the articulating surface 14 of the metal component 16. The optic system may include a controller having a control loop to monitor the surface finish of the articulating surface of the implant component and provide feedback for the controller to control the system. The loop may include a light source in the form of, for example, a laser that is used to direct an incoming beam onto the articulating surface of the implant component. The incoming beam from the light source is reflected by the articulating surface of the implant component and is redirected as a reflection beam to a light meter in the form of, for example, an optical processor.

It should be appreciated that, alternatively, the surface finishing measuring device 62 may utilize electrical conductivity to measure the surface finish of the articulating surface 14 of the metal component 16.

The device 10, as shown in FIG. 1, may further include a metal particle measuring device 64. The metal particle measuring device 64 may be utilized for measuring the content of metal particles 65 in the slurry 12. The metal particle measuring device 64 may include a light admitting device for admitting light onto the slurry. The metal particle measuring device 64 may further include a meter 66 for measuring the light reflected from the slurry. The metal particle measuring device 64 may measure one of the turbidity, the absorption or the reflectance of the slurry. It should be appreciated that the metal particle measuring device 64 may be utilized to measure the electrical conductivity of the slurry 12.

The device 10 may, as shown in FIG. 1, include a pad conditioning system 68 for conditioning the polishing pad 38. As the polishing pad 38 is utilized in the polishing zone 24 to improve the articulating surface 14 of the metal component 16, the metal from the metal component 16 as well as abrasive particles 32 from the slurry 12 build upon the polishing pad 38.

For optimum operation of the device 10, the polishing pad 38 may include the pad conditioning system 68 to remove the glaze or surface of the polishing pad 38 to expose the apertures 44 for containing the abrasive particles for proper operation of the device 10. The apertures 44 for the abrasive particles are exposed by conditioning the polishing pad 38 with the pad conditioning system 68 by the use of a tool, for example, a diamond tool 69 which is put in contact with the polishing pad 38 such that the polishing pad glazed surface is cleaned or machined.

Figure 2:
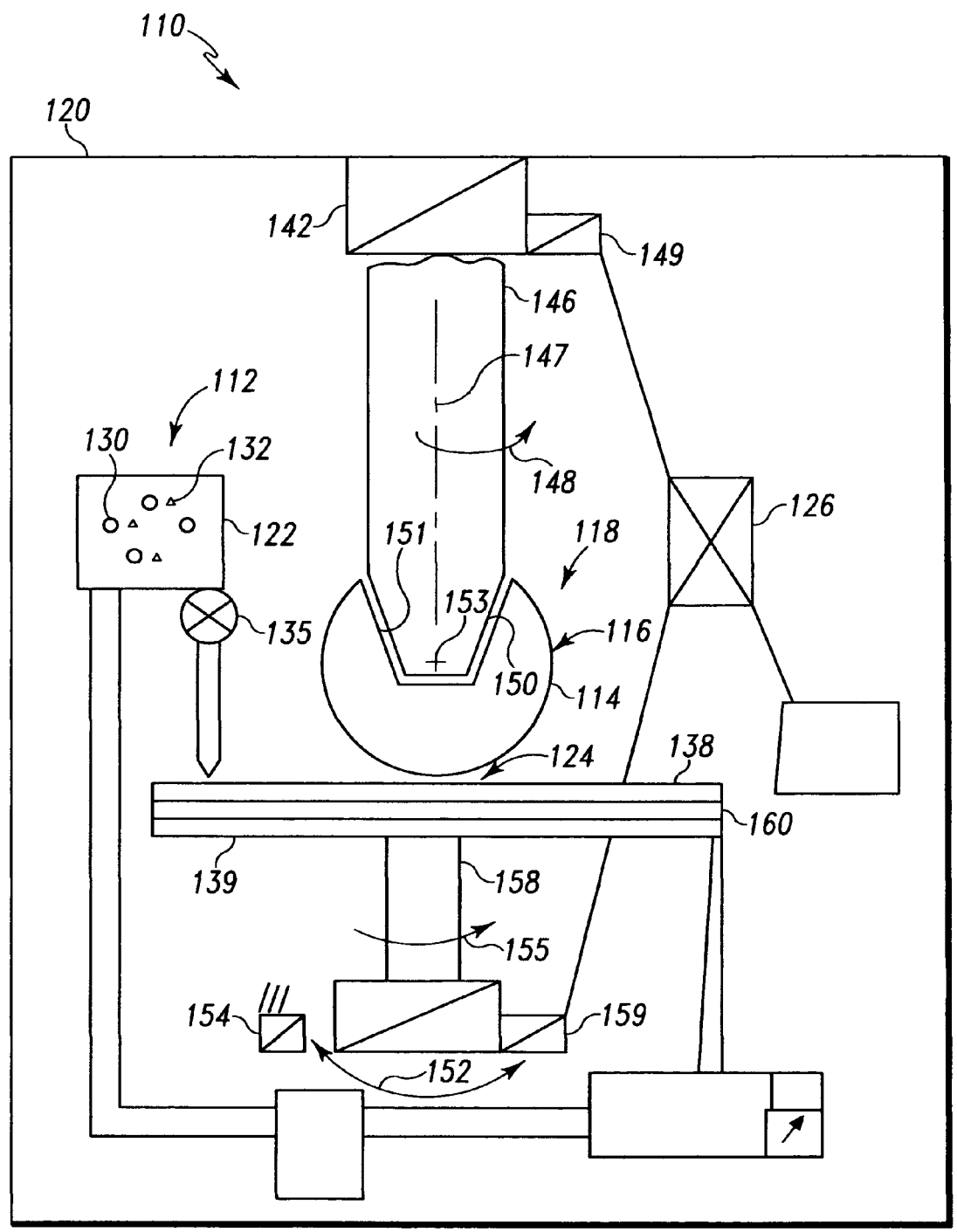
FIG. 2 is a schematic drawing of another polishing device for use to polish an orthopaedic hip head in accordance with another embodiment of the present invention.

According to the present invention, and referring now to FIG. 2, another embodiment of the present invention is shown as device 110. The device 110 of FIG. 2 is similar to the device 10 of FIG. 1 except that the device 110 includes a mechanism 126 which is somewhat different than the mechanism 26 of FIG. 1. The mechanism 126 includes a work piece mechanism 142 secured to frame 120 and a table mechanism 144 likewise secured to the frame 120 of the device 110.

The work piece mechanism 142 includes a spindle 146 which is positioned vertically and rotates about center line 147 and is drive by, for example, motor 149. The work piece mechanism, as is shown in FIG. 2, rotates in the direction of arrow 148 and has a fixture 150 in the form of an external tapered periphery which rotatably connects internal taper 151 of metal component in the form of hip head 116. The hip head 116 is a portion of orthopedic implant 118, for example, a hip prosthesis.

The table mechanism 144, as is shown in FIG. 2, is used to rotate table 139 in the direction of arrow 155. A platen or pressure plate 160 is positioned on the table 139 and a polishing pad 138 is positioned above the platen 160 and is in contact with the articulating surface 114 of the component or hip head 116 at polishing zone 124. The table mechanism 144 includes a table spindle 158 on which the table 139 is mounted. The table spindle 158 rotates in the direction of table arrow 155 and is rotated by, for example, motor 159. The table mechanism 144, unlike the table mechanism 44 of FIG. 1, also articulates to provide for the polishing of the entire articulating surface 114 of the hip head 116. For example, and as shown in FIG. 2, the table 139 articulates along arrow 152 about pivot point 153 and is articulated by, for example, an articulating motor 154.

The device 110 includes a vessel 122 which stores slurry 112 composed of chemical 130 mixed with abrasive particle 132. The slurry 112 is forced by pump 135 into the polishing zone 124 where the polishing pad 138 cooperates with the articulating surface 114 and the slurry 112 to prepare the articulating surface 114 of the hip head 116.

Figure 3:
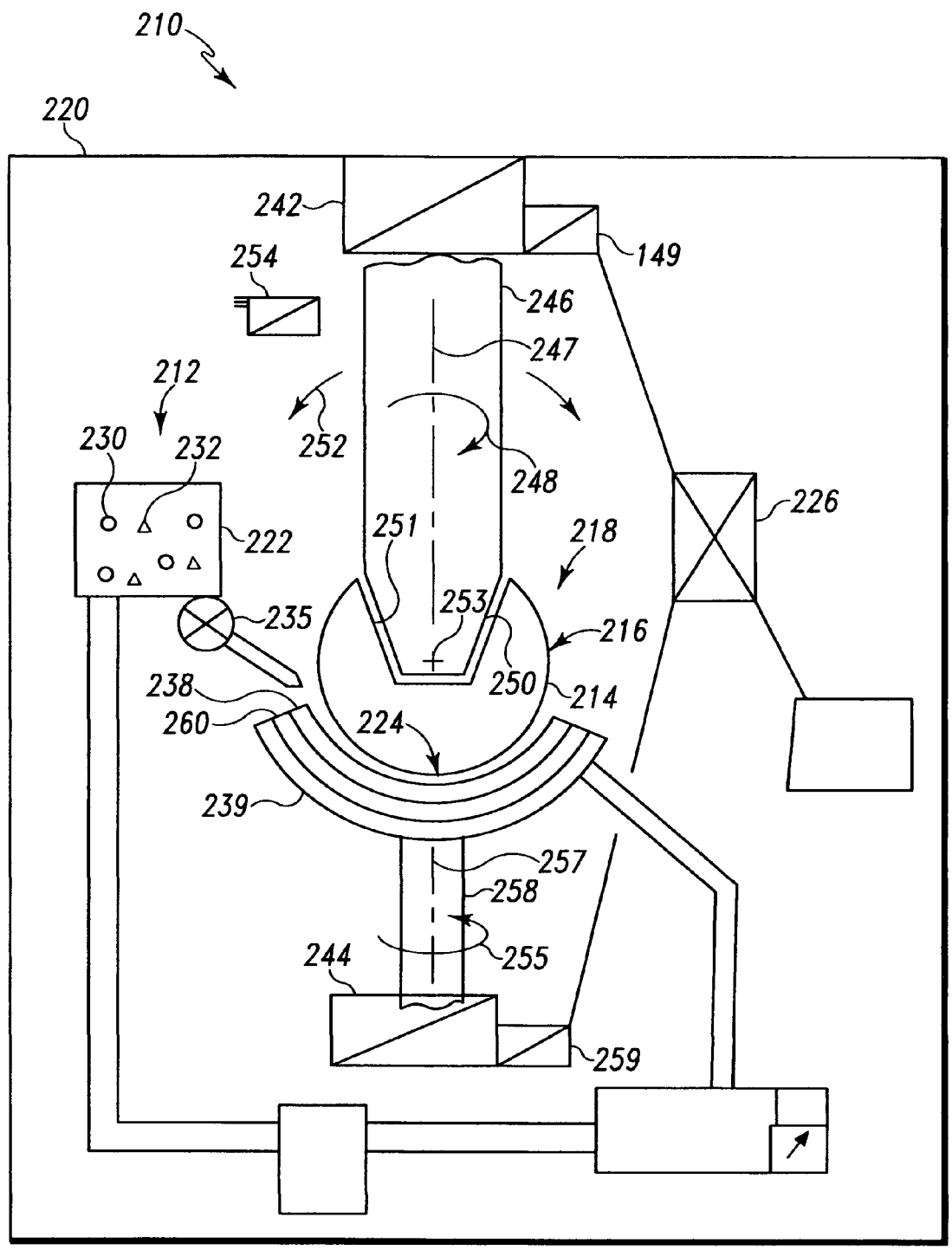
FIG. 3 is a schematic drawing of another polishing device for use to polish an orthopaedic hip head in accordance with another embodiment of the present invention.

Referring now to FIG. 3, yet another embodiment of the present invention is shown as device 210. The device 210 is similar to device 10 of FIG. 1, except that the device 210 includes a mechanism 226 which is somewhat different than the mechanism 26 of the device 10 of FIG. 1. The mechanism 226 includes a work piece mechanism 242 as well as table mechanism 244.

The work piece mechanism 242 includes a spindle 246 which is rotatably secured to frame 220 of the device 210. The spindle 246 rotates about center line axis 247 and is rotated for, by example, motor 249. The spindle 246 rotates in the direction of arrow 248 and includes a fixture 250 to which internal taper 251 of hip head 216 is fixedly secured. The spindle 246 of the work piece mechanism 242, as shown in FIG. 3, articulates along articulating arrow 252 and is driven by, for example, articulating motor 254 to expose the entire articulating surface 214 of hip head 216 to polishing pad 238.

The table mechanism 244 may include a spindle 258 which is fixedly secured to frame 220. It should be appreciated that the spindle 258 may be fixed, or may, as shown in FIG. 3, rotate about rotational center line 257 and rotate in the direction of, for example, arrow 255. The spindle 258 may be driven by, for example, motor 259. The spindle 258 supports table 239 to which platen 260 is secured. The platen or pressure plate 260 exerts a pressure on polishing pad 238 that contacts articulating surface 214 of the hip head 216. The polishing pad 238 contacts the articulating surface 214 of the hip head 216 in polishing zone 224. The polishing zone 224 includes slurry 212 which is contained within vessel 222. The slurry 212 includes a chemical 230 as well as abrasive particles 232. The slurry is forced by pump 235 into the polishing zone 224 to polish the articulating surface 214 of the hip head 216 of the orthopedic implant 218.

Figure 4:
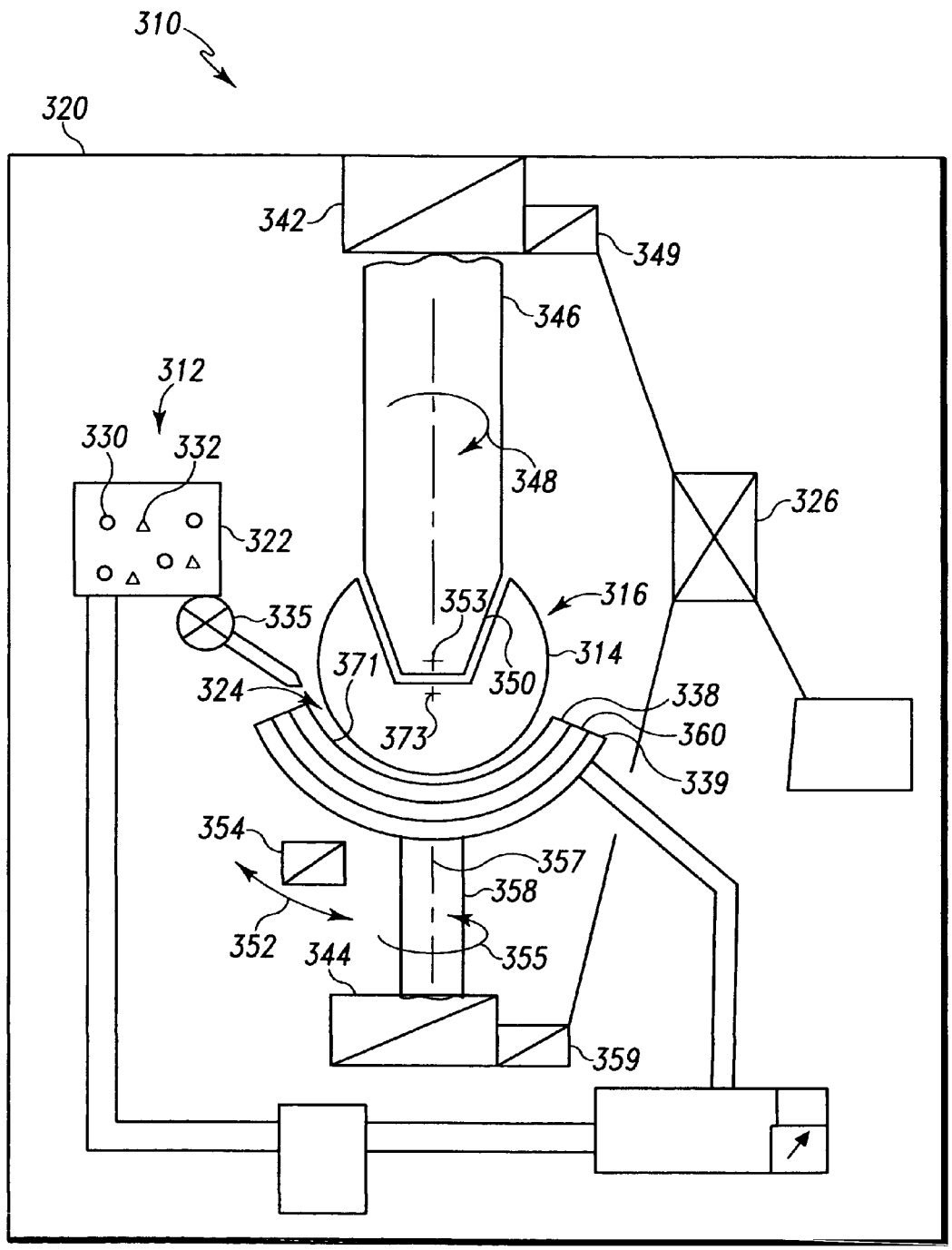
FIG. 4 is a schematic drawing of another polishing device for use to polish an orthopaedic hip head in accordance with another embodiment of the present invention.

Referring now to FIG. 4, yet another embodiment of the present invention is shown as device 310. The device 310 is similar to the device 210 in that the device 310 includes a polishing pad 338 that is arcuate. The device 310 includes a work mechanism 326 which includes a work piece mechanism 342 as well as table or pad mechanism 344.

The work piece mechanism 342 includes a spindle 346 which is rotatably secured to frame 320 of the device 310. The spindle 346 rotates in the direction of arrow 348 about center line 347 and is driven by, for example, motor 349. The spindle 346 includes a fixture 350 to which hip head 316 is fixedly secured. The hip head 316 includes an articulating surface 314 which is to be polished by the device 310.

The table mechanism 344 includes a spindle 358 which may be fixed or may rotate in, for example, the direction of arrow 355 along center line 357. The spindle 358 may be rotated, for example, by motor 359. The spindle 358 supports table 339 to which platen 360 is secured. The pad 338 is supported by the platen 360.

The pad 338, as shown in FIG. 4, has an arcuate or concave surface 371 in which the slurry 312 may be placed. The concave surface 371 may serve as vessel 322. The concave surface 371 may be defined by radius RP extending from origin 373 which may be coincident with pivoting point 353. The internal periphery 371 of the pad 338 may extend around the entire articulating surface 314 of the hip head 316 or, as shown in FIG. 4, the pad 338 may rotate around pivot point 353 and be rotated along arrow 352 by articulating motor 354.

Slurry 312 contained within vessel 322 may include a chemical 330 as well as abrasive particles 332. Slurry 312 may be advanced by pump 335 toward polishing zone 324 between the articulating surface 314 and the pad 338.

While it should be appreciated that the device of the present invention may be utilized to polish hip heads, it should be appreciated that the device of the present invention may be utilized to finish any articulating surface of an orthopedic implant. For example, and referring now to FIG. 5, another embodiment of the present invention is shown as device 410.

Device 410 is similar to device 10 of FIG. 1 except that the device 410 is utilized for polishing a metal orthopedic implant in the form hip cup 416. The hip cup 416 includes an articulating surface 414 in the form of a concave surface defined by radius Rc extending from origin 473.

The device 410 includes a frame 420 to which mechanism 426 is attached. The mechanism 426 includes a polishing pad mechanism 442 as well as a work piece mechanism 444. The work piece mechanism 444 includes a fixture 450 on which hip cup 416 is secured. A pressure plate 460 is secured to pad spindle 450 of pad mechanism 442.

The work piece mechanism 444 includes a work piece spindle 446 that is secured to the frame 420. The work piece spindle 446 is rotated about center line 447 by, for example, a motor 449. The work piece spindle, as shown in FIG. 5, may rotate about a fixed center line 447 or, as is shown in FIG. 5, may pivot about pivot point 453.

Figure 5:
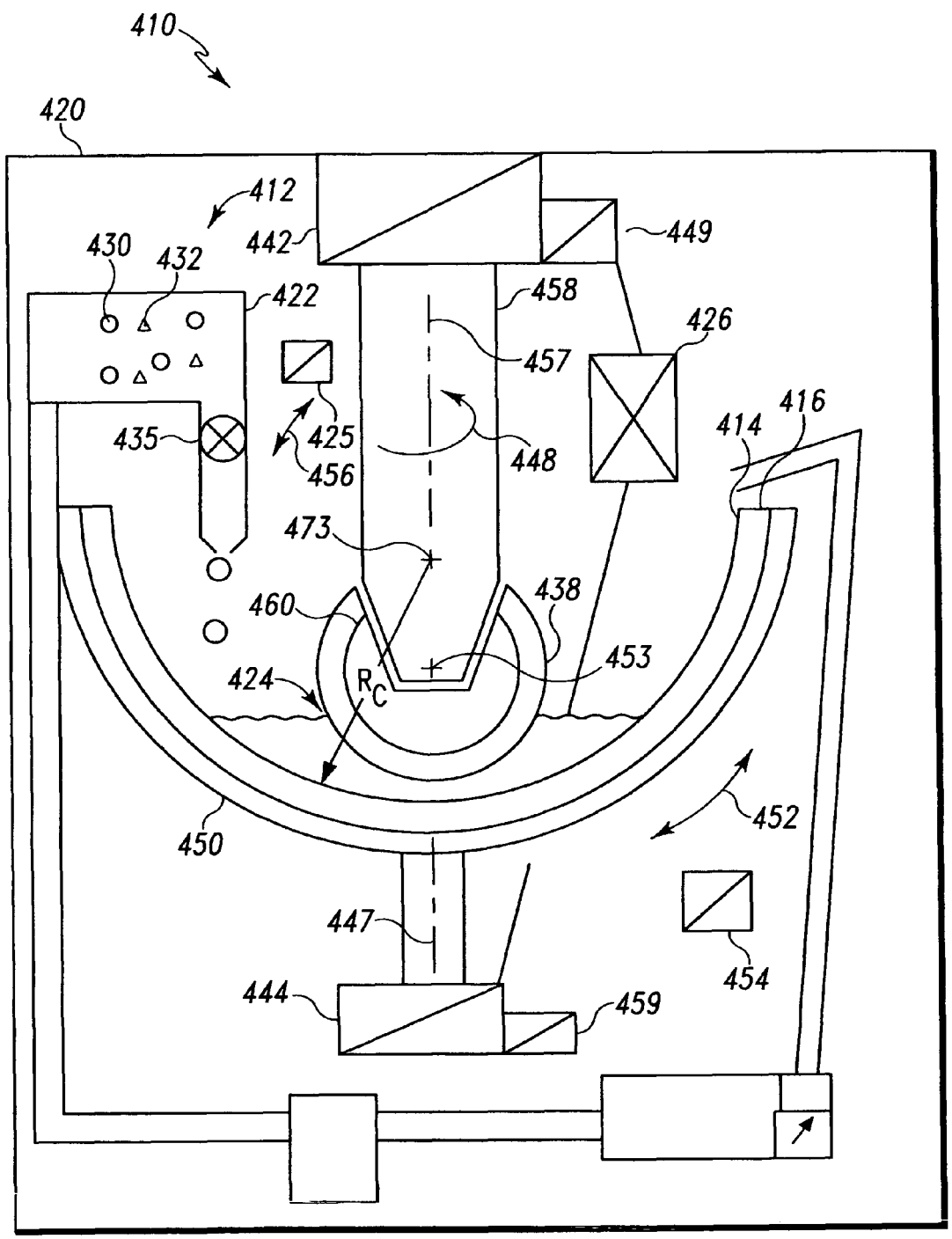
FIG. 5 is a schematic drawing of another polishing device for use to polish an orthopaedic hip cup in accordance with another embodiment of the present invention.

As shown in FIG. 5, the work piece spindle 446 may articulate in the direction of arrow 452 and be the articulated by articulation motor 454. The fixture 450 may be secured to the work piece spindle 456 and may be utilized to secure the hip cup 416.

The pad mechanism 442 may include a pad spindle 458 which rotates by spindle motor 459 about table spindle rotational axis 457. The pad spindle 458 may rotate in, for example, the direction of arrow 448. While the pad spindle 458 may rotate about a constant vertical axis 457, it should be appreciated to polish the entire articulating surface 414 of the hip cup 416, the axis 457 of the table spindle 458 may articulate about axis 453 in the direction of arrows 456 by, for example, articulation motor 475.

The pad spindle 458 may support, for example, polishing pad 438 which contacts the articulating surface 414 of the hip cup 416 in polishing zone 424. A slurry 412 including chemical 430 and abrasive particles 432 may be pumped by, for example, pump 435 toward polishing zone 424.

As shown in FIG. 5, the slurry 412 is delivered to the polishing zone 424 where it is contained in vessel 422. The vessel 422 may be a separate structure or the hip cup 416 may serve as the vessel for containing slurry 412 within the polishing zone 424.

Figure 6:
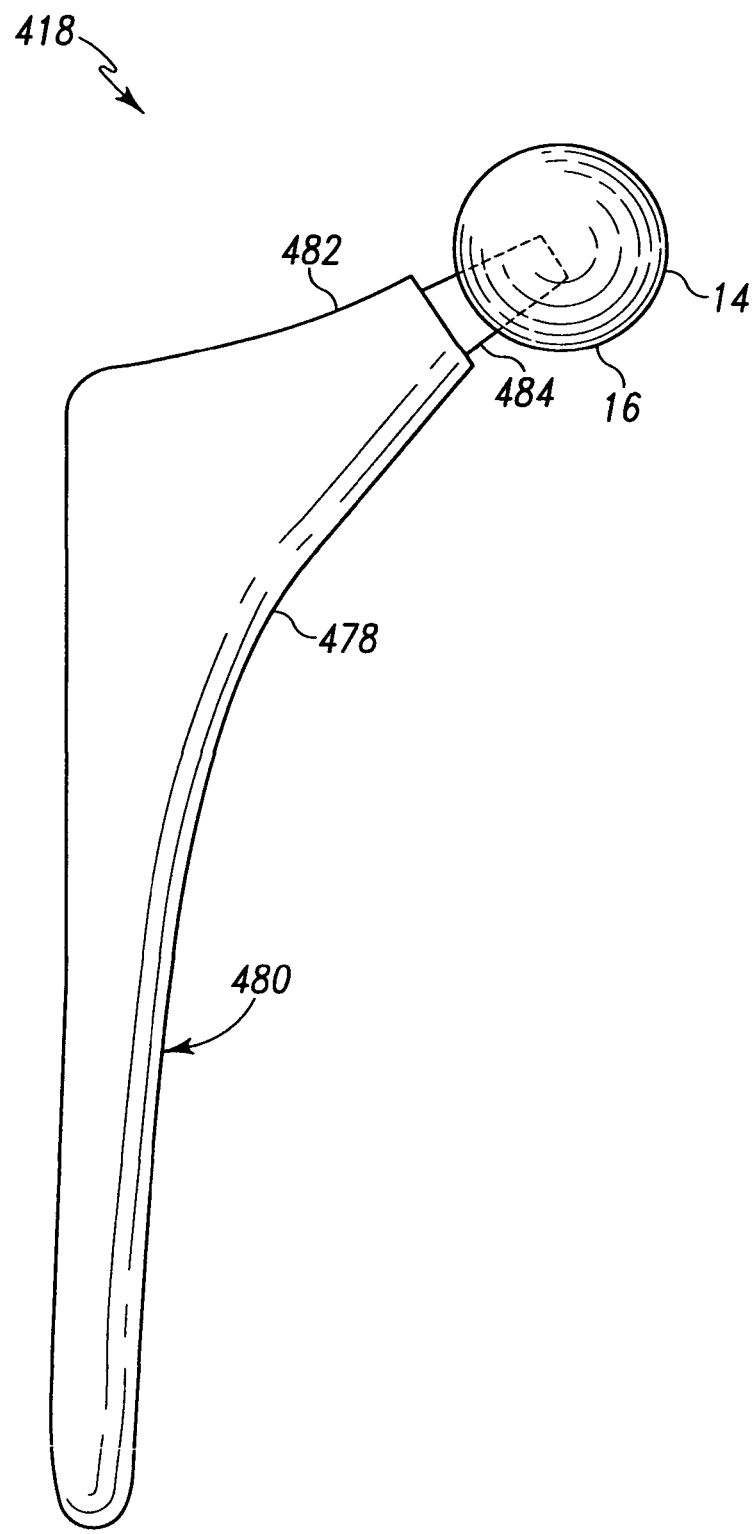
FIG. 6 is a plan view, partially in cross section, of a hip stem with an articulating head that may be polished with the polishing device of an embodiment of the present invention.

Referring no to FIG. 6, the stem assembly of the hip prosthesis 418 is shown. The hip prosthesis 418 includes the hip head 16 including the articulating surface 14 as well as hip stem 478 to which the head 16 is attached. The stem 478 includes a distal stem 480 and a proximal neck 482 as well as a protrusion 484 to which the head 16 is attached.

Figure 7:
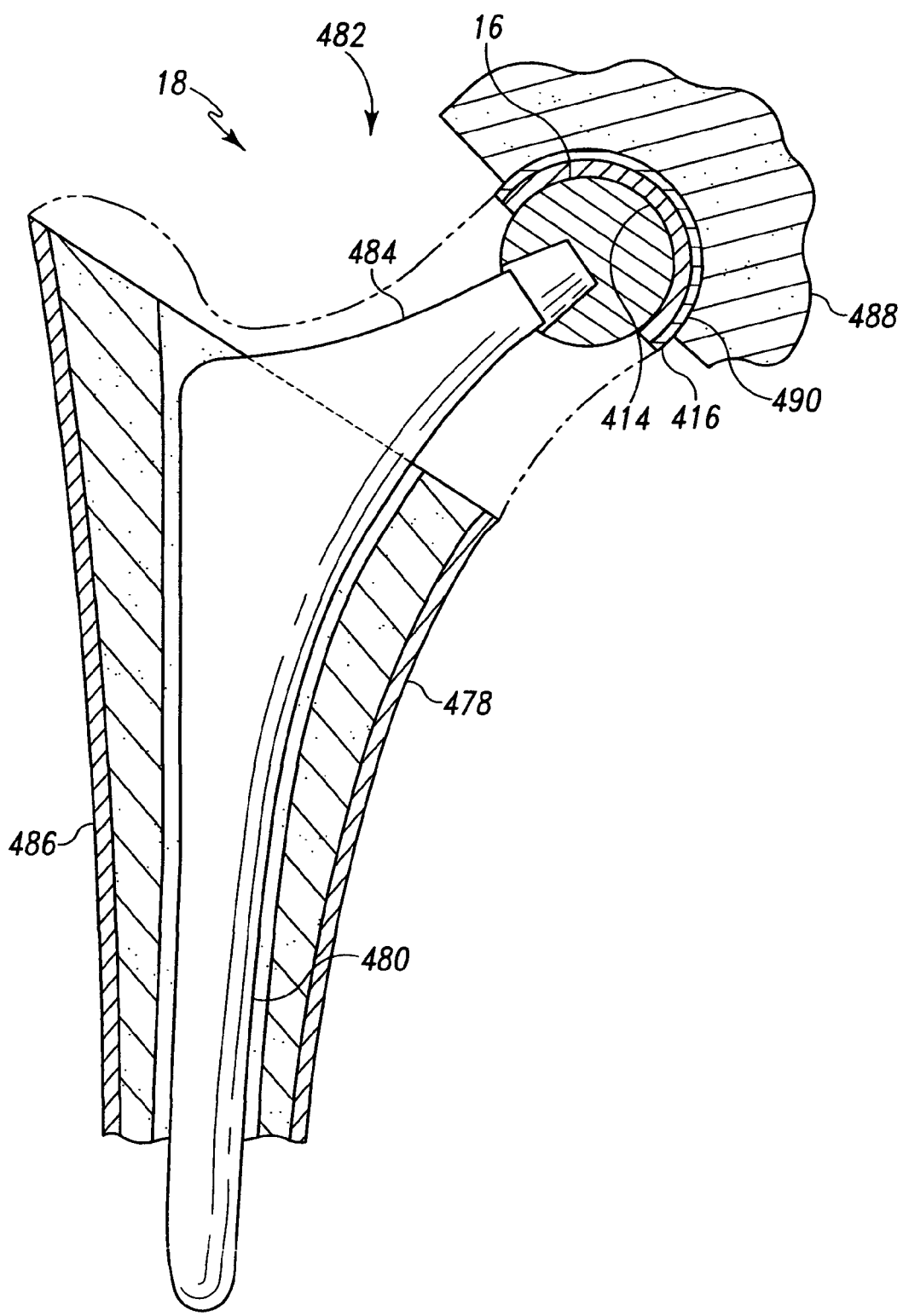
FIG. 7 is a plan view of the hip stem of FIG. 6 implanted in a femur with a hip cup with an articulating surface that may be polished with the polishing device of an embodiment of the present invention.

Referring now to FIG. 7, the entire hip prosthesis 18 is shown. The hip prosthesis 418 includes the stem 478 including the distal stem 480 which is secured in cavity 482 formed in canal 484 of long bone or femur 486.

A hip cup 416 including articulating surface 414 is secured to acetabulum 488. While the hip cup 416 may directly contact the head 16, it should be appreciated that a bearing or liner 490 may be positioned between the head 16 and the cup 416.

While the device of the present invention may, as shown in FIGS. 1-5, be utilized for a hip prosthesis, it should be appreciated that the device of the present invention may be utilized for other joints within the human anatomy. For example, and referring now to FIGS. 8-11, the device of the present invention may be utilized to polish components of a shoulder prosthesis.

Figure 8:
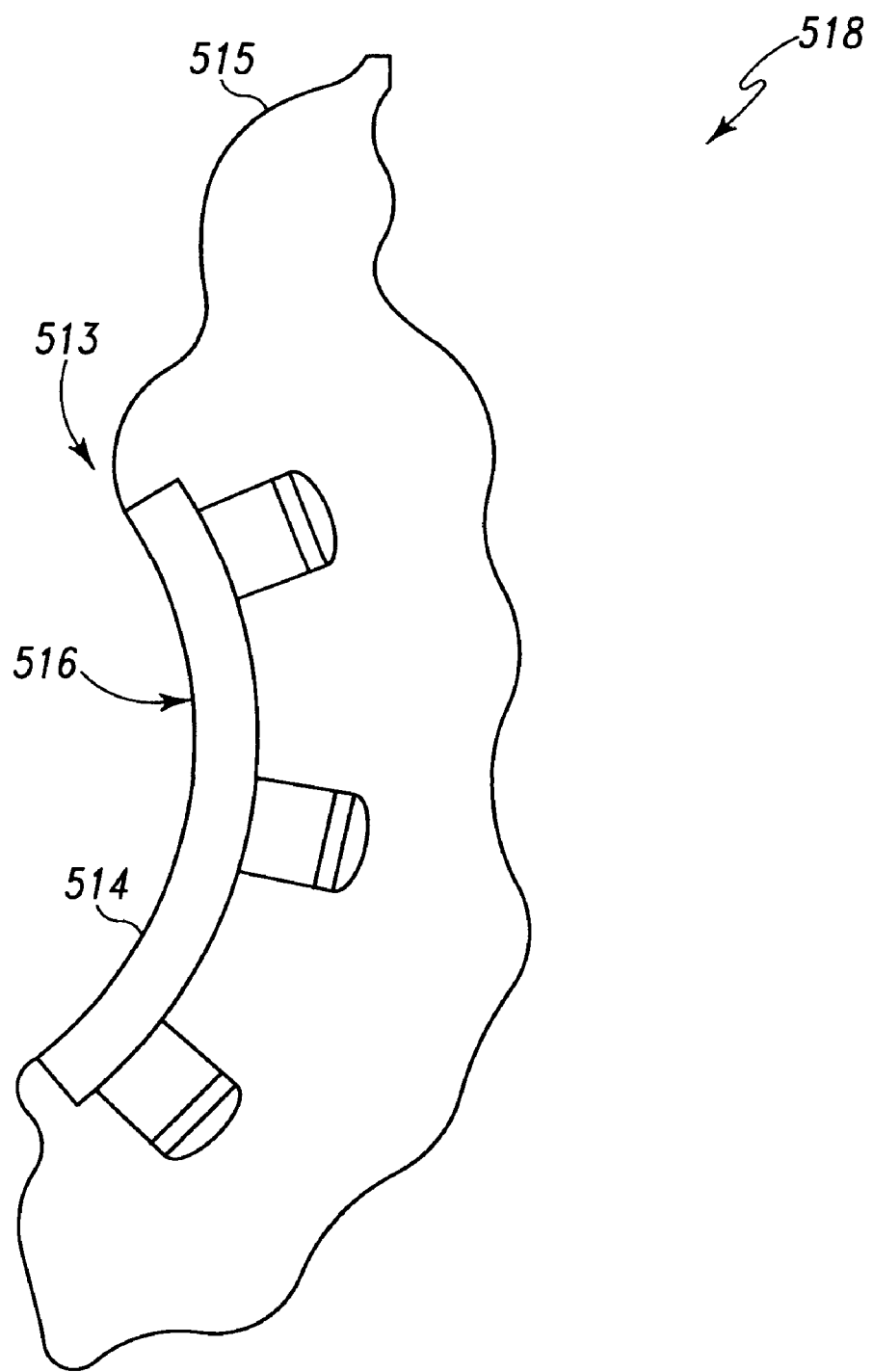
FIG. 8 is a plan view, partially in cross section, of a glenoid component of a shoulder prosthesis with an articulating surface that may be polished with the polishing device of an embodiment of the present invention.

Referring now to FIG. 8, a shoulder prosthesis 518 is shown. The device of the present invention may be utilized to polish the articulating surface of the shoulder prosthesis 518. The shoulder prosthesis 518 includes a glenoid component 516 including a concave articulating surface 514. The glenoid component 516 is secured to, for example, glenoid cavity 513 formed in scapula 515.

Referring now to FIG. 8, yet another embodiment is shown in the form of device 510. The device 510 is adapted to polish the articulating surface 514 of the glenoid component 516 of the shoulder prosthesis 518. The device 510 includes a mechanism 526 that is secured to frame 520 of the device 510. The mechanism 526 includes a work piece mechanism 542 and a table mechanism 544.

Figure 9:
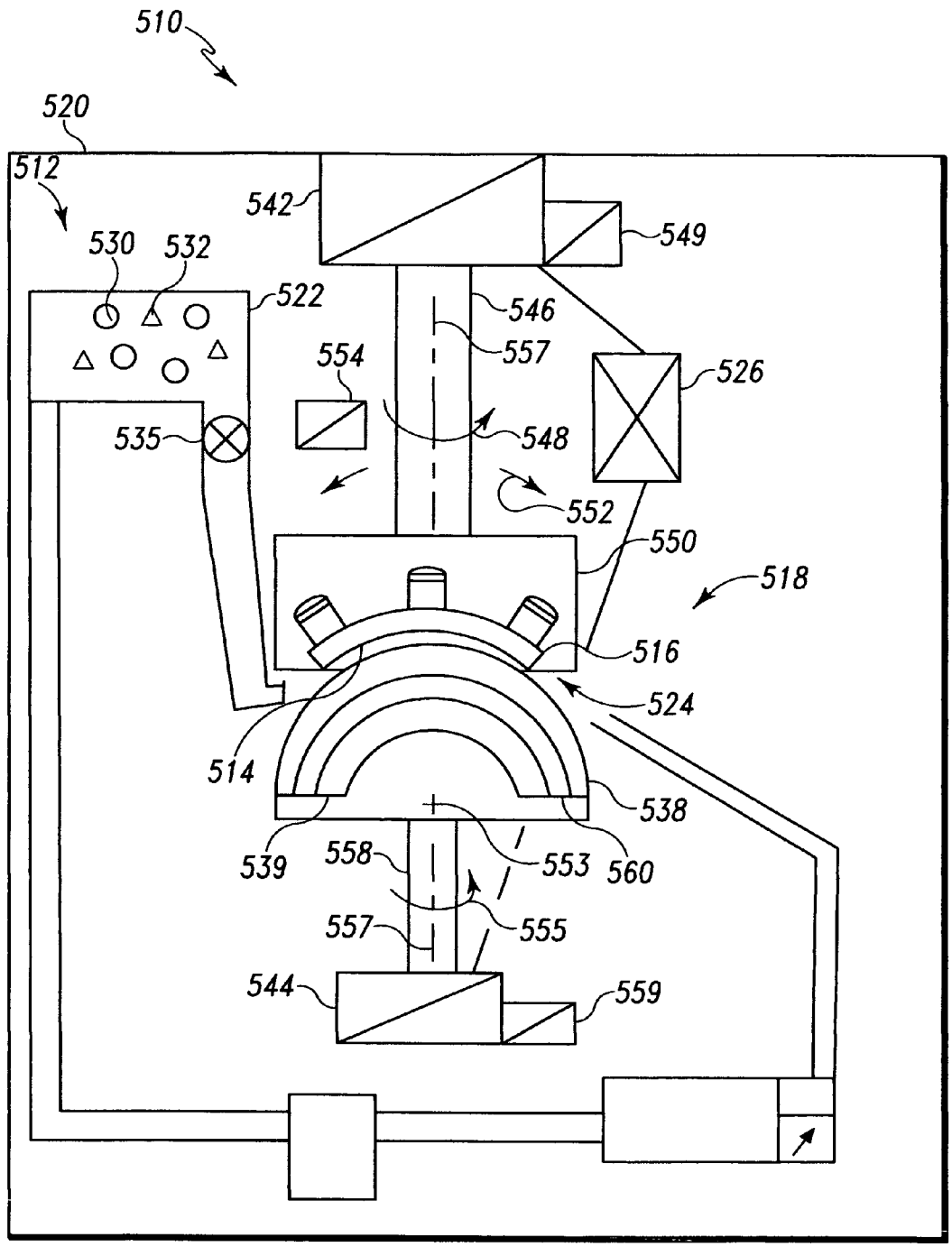
FIG. 9 is a schematic drawing of a polishing device for cooperation with the articulating hemispherical periphery of the glenoid component of FIG. 8 in accordance with another embodiment of the present invention.

The work piece mechanism 542 includes a work piece spindle 546 that rotates in the direction of arrow 548 about work piece spindle center line 547. The work piece spindle 546 is rotated by, for example, work piece spindle motor 549. The work piece spindle 546 supports fixture 550. The fixture 550 is adapted to secure glenoid component 516 to the fixture 550. The glenoid component 516 may rotate about a constant work spindle center line 547 or, as shown in FIG. 8, rotate about pivot point 553 such that the entire articulating surface 514 of the glenoid component 516 may be polished. For example, and as shown in FIG. 9, the work piece mechanism 542 further includes a articulation motor 554 which rotates or articulates the work piece spindle 546 in the direction of articulation arrows 552.

The table mechanism 544 includes a table spindle 558 which rotates in the direction of arrow 555 about table spindle center line 557. The table spindle 558 is rotated by, for example, spindle motor 559. The table spindle 558 supports a table 539 to which pressure plate 560 is secured. A polishing pad 538 is secured to the pressure pad 560. The pressure plate 560 urges the pad 538 against articulating surface 514 of the glenoid component 516.

The device 510 further includes a slurry 512 which is a combination of a chemical 530 and abrasive particles 532. The slurry 512 is advanced by, for example, pump 535 toward polishing zone 524. The slurry 512 is contained by, for example, vessel 522 to contain the slurry 512 within the polishing zone 524.

Figure 10:
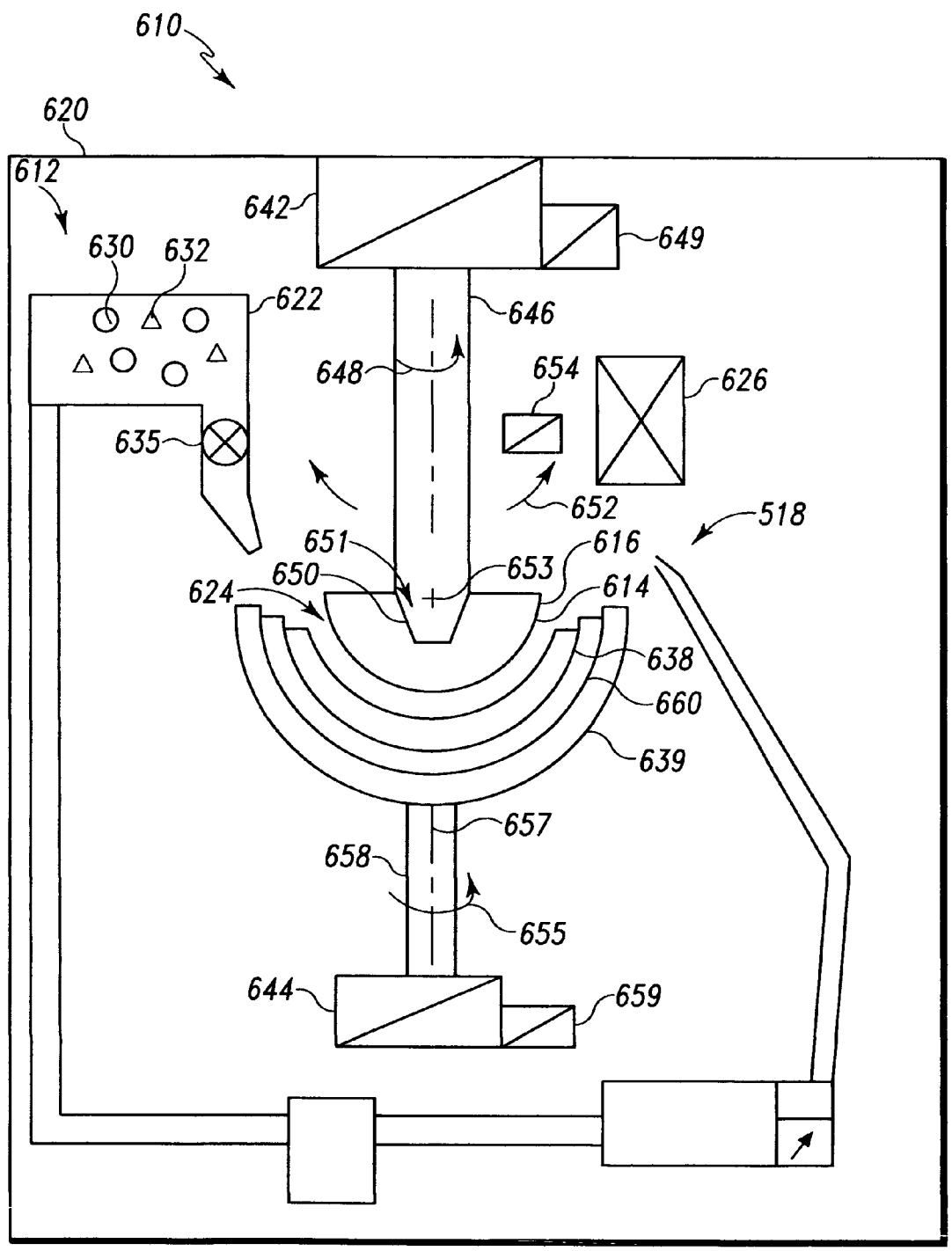
FIG. 10 is a schematic drawing of another polishing device for use in performing shoulder orthopaedic surgery in accordance with yet another embodiment of the present invention.

Referring now to FIG. 10, device 610 according to the present invention is shown. The device 610 is used for polishing articulating surface 614 of shoulder stem head 616. The shoulder stem head 616 is a part of shoulder prosthesis 518. The device 610 includes a mechanism 626 connected to frame 620. The mechanism 626 includes a work piece mechanism 642 and a table mechanism 644. The work piece mechanism 642 includes a work piece spindle 646 which rotates about vertical center line 647 in the direction of arrows 648. The work piece spindle 646 is driven by work piece spindle motor 649.

To assure that the entire articulating surface 614 of the shoulder stem head 616 is polished, the work piece spindle 646 may have a mechanism such that vertical center line 647 of the spindle 646 articulates about pivot point 653. Work piece spindle 646 articulates along the direction of articulation arrows 652 and is articulated by, for example, articulation motor 654. The workpiece spindle 646 includes a fixture 650 in the form of an external taper which mates with internal taper 651 of the shoulder stem head 616.

The table mechanism 644 includes a table spindle 658 which is rotatably fixed to frame 620. The table spindle 658 is rotated along spindle center line 657 and is rotated in the direction of arrow 655, by motor 659. A table 639 is supported by the table spindle 658. A pressure plate, or platen, 660 is supported by the table 639. A pad 638 is positioned between the pressure plate 660 and the shoulder stem head 616. The The device 610 includes a slurry 612 comprised of chemical 630 as well as abrasive particles 632. The slurry 612 is moved by pump 635 to polishing zone 624 positioned between the articulating surface 614 of the head 616 and the pad 638. A vessel 622 contains the slurry 612 in the polishing zone 624. It should be appreciated that the concave shape of the pad 638 may serve as a vessel or a separate vessel encapsulating the pad 638 may be used. The pad 638 is concave to match the convex shape of the articulating surface 614 of the shoulder stem head 616.

Figure 11:
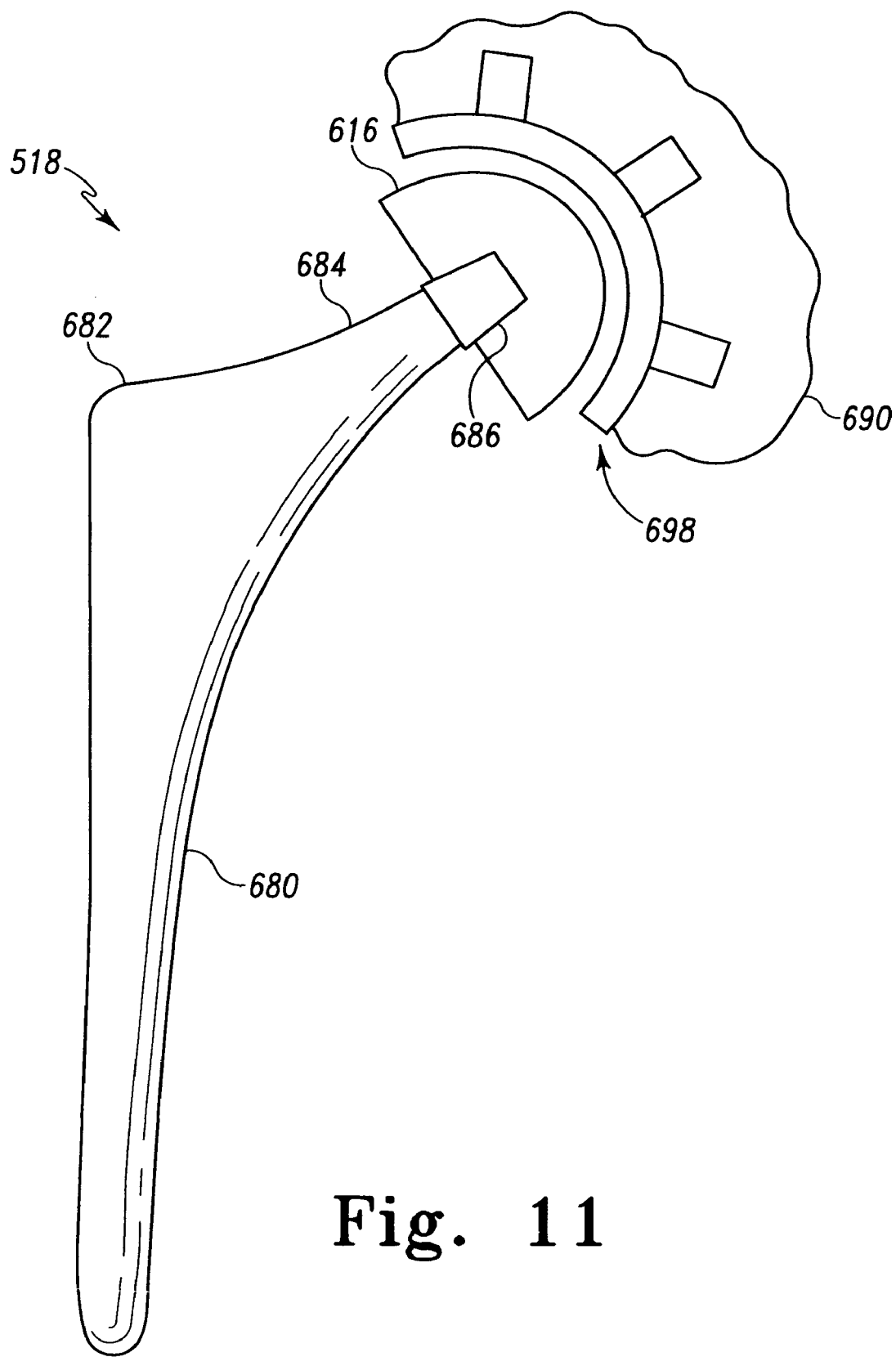
FIG. 11 is a plan view of a humeral implant for use in performing shoulder orthopaedic surgery with components that may be machined with the devices of FIGS. 8 and 10.

Referring now to FIG. 11, shoulder prosthesis 518 for use with the devices 510 and 610 of FIGS. 9 and 10, respectively, is shown. The shoulder prosthesis 518 includes the humeral head 616 that may be polished by the device 610 of FIG. 10 and the glenoid component 516 that may be polished by device 510 of FIG. 9. The shoulder prosthesis 518 includes humeral stem 682 which includes a distal stem 680 as well as neck 684 extending from distal stem 680. The humeral stem 682 further includes a protrusion 686 extending outwardly from the neck 684. Humeral head 616 is secured to protrusion 686 of the humeral stem 682. The glenoid component 516 is secured to glenoid cavity 688 of scapula 690.

Figure 12:
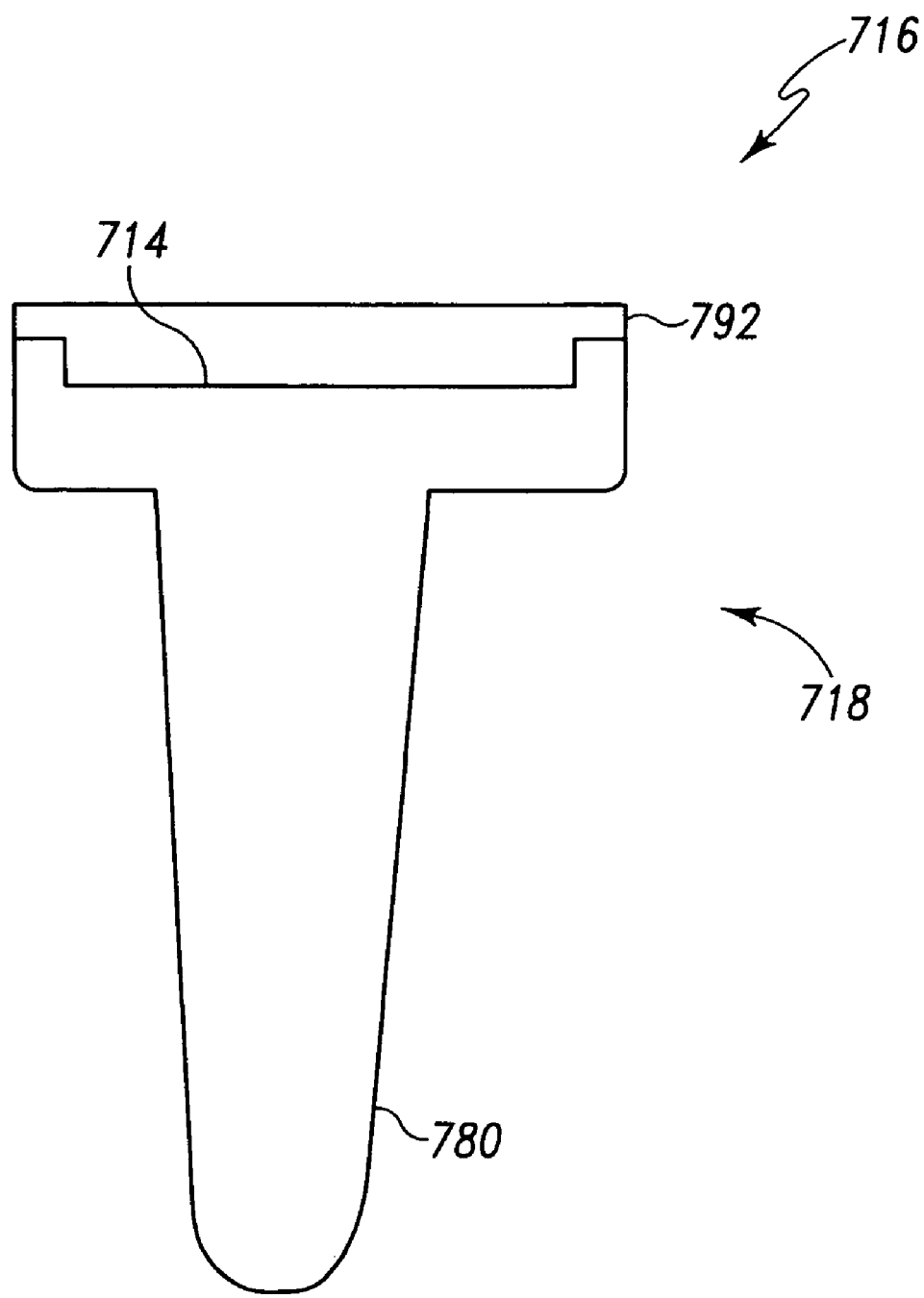
FIG. 12 is a plan view, partially in cross section, of a tibial tray component with recessed face of a knee prosthesis for use with the polishing device of another embodiment of the present invention.

Referring now to FIG. 12, a knee orthopedic prosthesis 718 that may be polished utilizing the device of the present invention is shown. The knee prosthesis 718, as shown in FIG. 12, includes a tibial tray 716 which includes an articulating surface 714 which extends from stem 780 of the tibial try 716. An articulating tray 792 is rotatably secured to the tibial tray 716.

Figure 13:
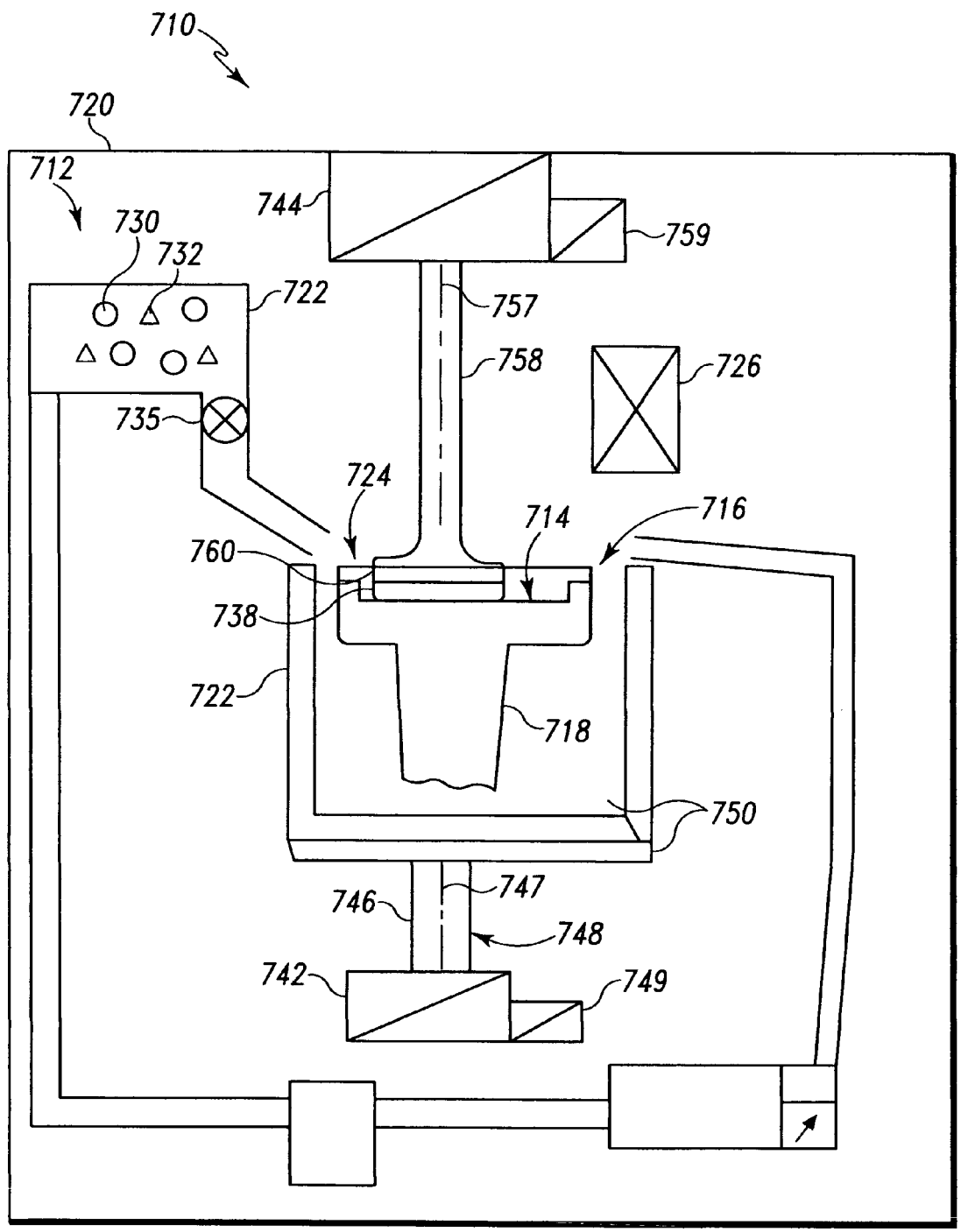
FIG. 13 is a schematic drawing of a polishing device for cooperation with the articulating periphery of the tibial tray component of FIG. 12 in accordance with another embodiment of the present invention.

Referring now to FIG. 13, yet another embodiment of the present invention is shown as device 710. Device 710 of FIG. 13 is similar to the device 10 of FIG. 1 except that the device 710 of FIG. 13 is utilized for polishing articulating surface 714 of tibial tray 716.

The device 710 includes a mechanism 726. The mechanism 726 includes a work piece mechanism 742 and a pad mechanism 744. The work piece mechanism 742 is positioned below the pad mechanism 744. The work piece mechanism 742 includes a work piece spindle 746 that rotates in the direction of arrow 748 and is driven by work piece motor 749 about work piece spindle center line 747. The work piece spindle 746 is connected to fixture 750 which supports the tibial tray 716. The tibial tray 716 is located in, for example, vessel 722 for containing slurry 712 which is located in the polishing zone 724.

The pad mechanism 744 includes a pad spindle 758 rotatably secured to the frame 720. The pad spindle 758 rotates about spindle center line 757 and rotates in the direction of arrow 755 and is rotated by pad motor 759. A pump 735 is used to delivery the slurry 712 including chemical 730 and abrasive particles 732 to polishing zone 724 positioned between the articulating surface 714 of the tibial tray 716 and pad 738 secured to the pressure plate 760 which is rotated by pad spindle 758.

Figure 14:
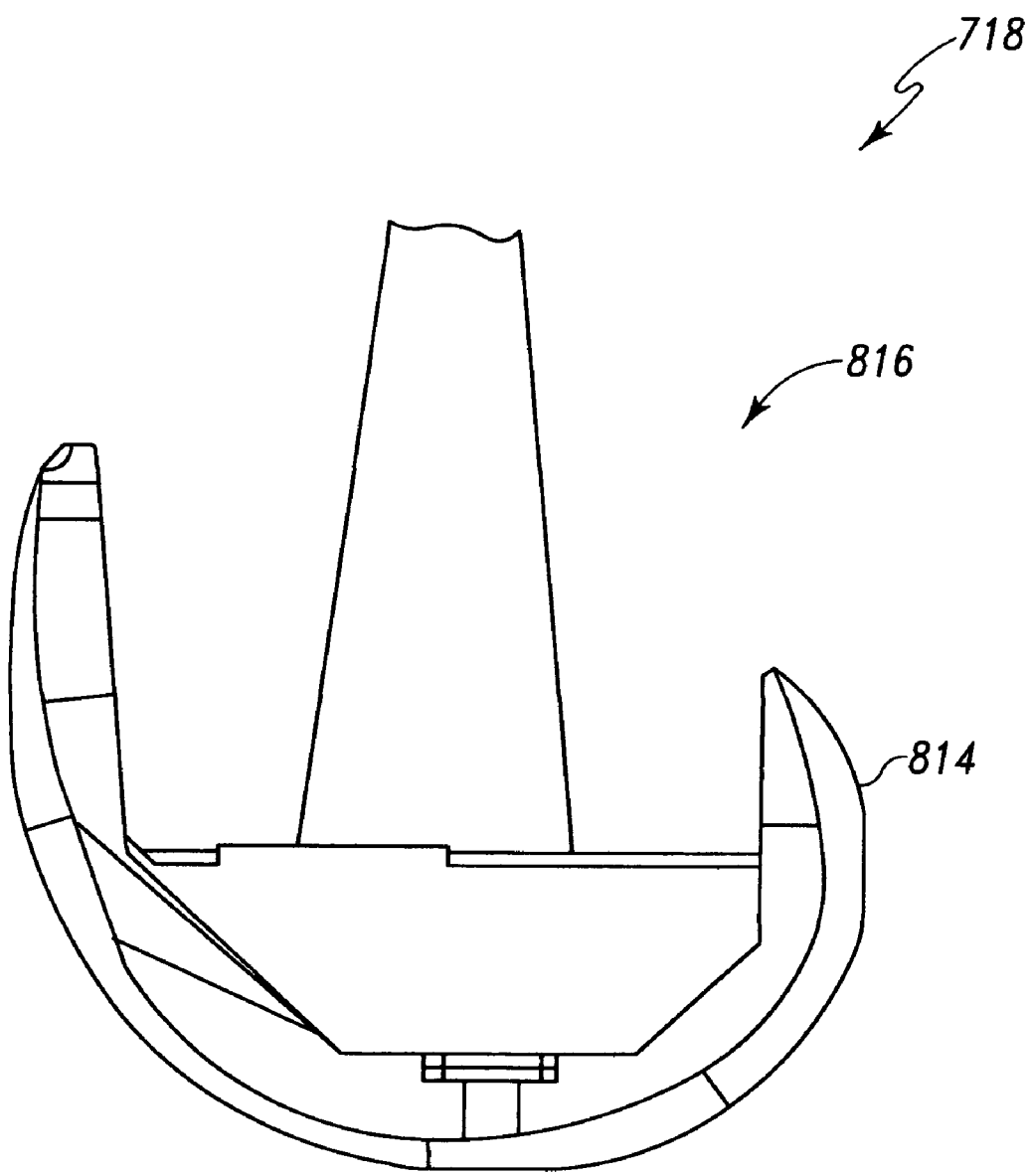
FIG. 14 is a plan view, partially in cross section, of a femoral component of a knee prosthesis for use with the polishing device of another embodiment of the present invention.

Referring now to FIG. 14, yet another prosthetic component that may have an articulating surface polished by a device of the present invention is shown. As shown in FIG. 14, femoral component 816 of knee prosthesis 718 includes articulating surface 814.

Figure 15:
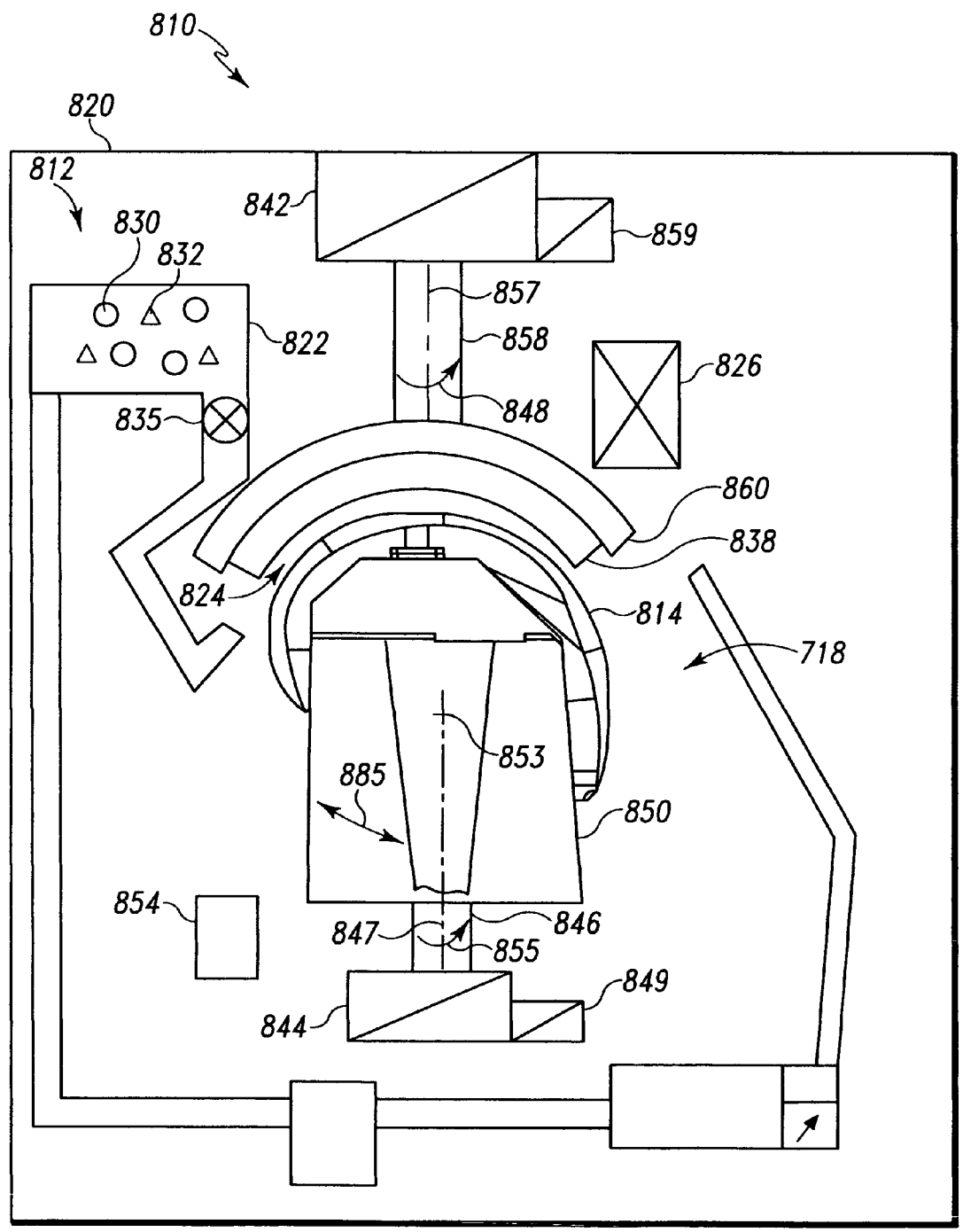
FIG. 15 is a schematic drawing of a polishing device for cooperation with the articulating periphery of the femoral component of FIG. 12 in accordance with another embodiment of the present invention.

Referring now to FIG. 15, yet another embodiment of the present invention is shown as device 810. The device 810 of FIG. 15 is like the device 10 of FIG. 1 except that the device 810 of FIG. 15 includes a mechanism 826 which may accommodate femoral component 816 of the knee prosthesis 718. The device 810 polishes articulating surface 814 of femoral component 816. The mechanism 826 of the device 810 includes a pad mechanism 842 for rotating pressure plate 860 and pad 838, as well as, work piece mechanism 844 for positioning the articulating surface 814 of the femoral component 816.

The work piece mechanism 844 includes a work piece spindle 846 that is rotatably secured to frame 820 of the device 810. The work piece spindle 846 rotates in the direction of arrows 855 along work piece center line 847 by work piece motor 849. The work piece mechanism 844, as shown in FIG. 15, further includes an articulating motor 854 which articulates the femoral component 816 about pivot point 853 in the direction of articulating arrows 852. The work piece spindle 846 supports a fixture 850 which secures the femoral component 816 to the work piece spindle 846.

A vessel 822 contains slurry 812 in polishing zone 824 positioned between the articulating surface 814 of the femoral component 816 and the table 839.

The pad mechanism 842 includes a pad spindle 858 rotatably secured to frame 820. The pad spindle 858 rotates about pad center line 857 in the direction of arrows 848 by, for example, pad motor 859. A pressure plate 860 is secured to the pad spindle 858 and a pad 838 is secured to pressure plate 860. The pad 838 is in contact with articulating surface 814 of the femoral component 816 in the polishing zone 824. The slurry 812 including a chemical 830 and an abrasive particle 832 is moved by, for example, pump 835 toward the polishing zone 824.

Figure 16:
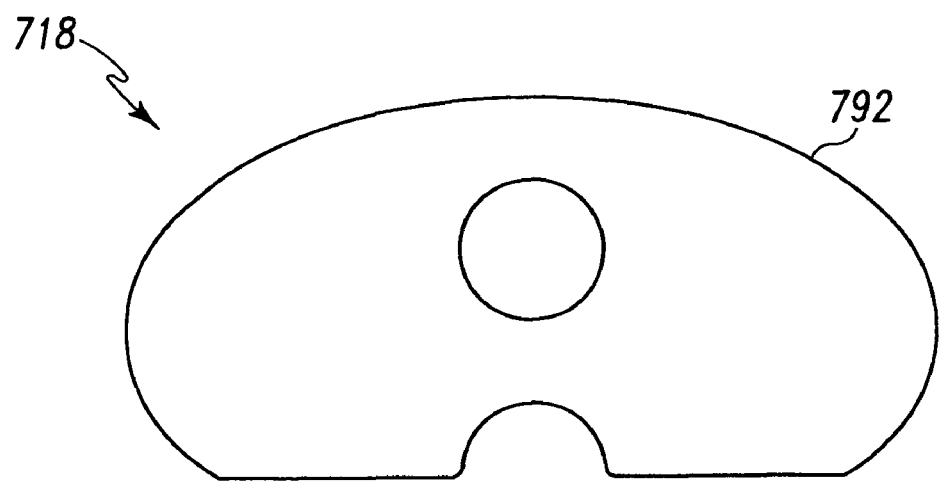
FIG. 16 is a top view of a knee tibial tray for use in performing orthopaedic surgery that may be machined in accordance with yet another embodiment of the present invention.
Figure 17:
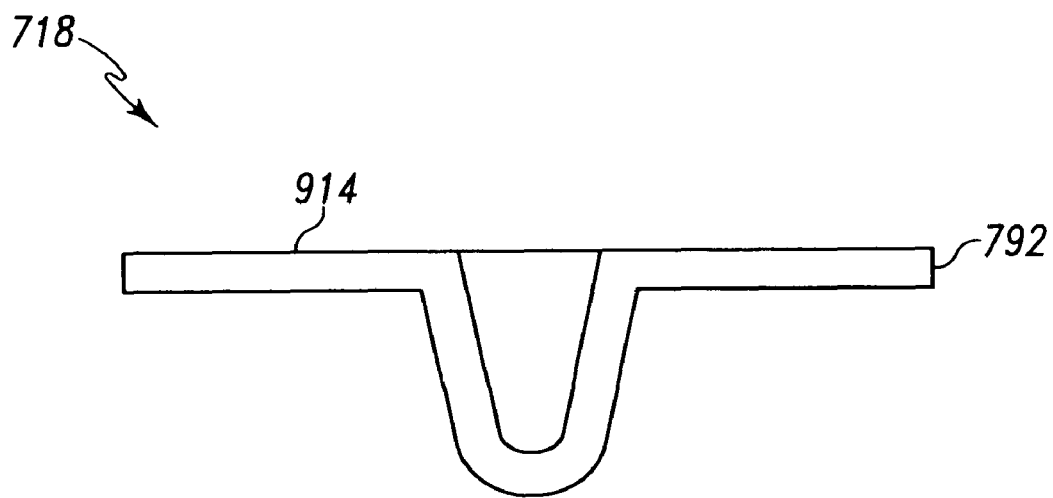
FIG. 17 is a plan view of the knee tibial tray of FIG. 16.

Referring now to FIGS. 16 and 17, the rotating platform of the knee prosthesis is shown in greater detail. As shown in FIGS. 16 and 17, rotating tray 792 of knee prosthesis 718 is shown in greater detail. The tray 792 includes an articulating surface 914. The articulating surface 914 may be polished by a device 910 according to the present invention.

Figure 18:
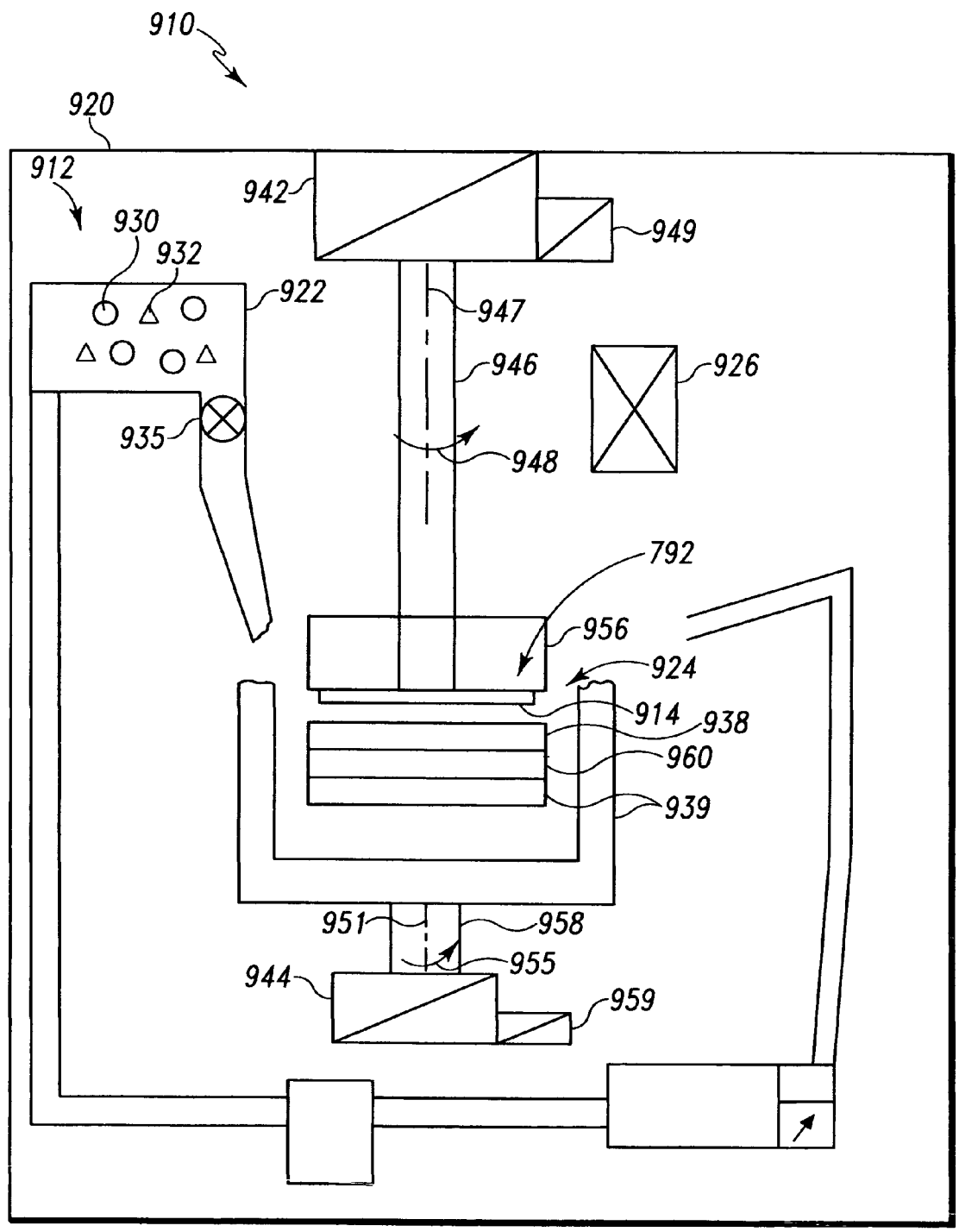
FIG. 18 is a schematic drawing of a polishing device for cooperation with the bearing surface of the knee tibial tray of FIG. 17.

Referring now to FIG. 18, yet another embodiment of the present invention is shown as device 910. The device 910 of FIG. 18, is similar to the device 10 of FIG. 1 except that the device 910 is utilized to polish articulating surface 914 of the tray 792. The device 910 includes a mechanism 926 for assisting in polishing the articulating surface 914 of the tray 792. Mechanism 926 includes a work piece mechanism 942 and a table mechanism 944.

The work piece mechanism 942 is used to support the work piece or tibial tray 792. The work piece mechanism 942 includes a work piece spindle 946 that is rotatably secured to frame 920 of the device 910. The work piece spindle 946 rotates in the direction of arrow 948 about spindle center line 947 and is rotated by, for example, motor 949. A fixture 950 is secured to the work piece spindle 946. The fixture 950 secures the tibial tray 792 to the fixture 950 and to the work piece spindle 946.

The table mechanism 944 includes a table spindle 958 which is rotatably secured to the frame 920. The spindle 958 rotates about spindle vertical center line 957 in the direction of arrow 955. The spindle 958 is rotated by, for example, spindle motor 959. The spindle 958 supports table 939. A pressure plate 960 is secured to the table 939. An abrasive pad 938 is secured to the pressure plate 960. Slurry 912 including a chemical 930 and an abrasive particle 932 is positioned over pad 938 in polishing zone 924 between the pad 938 and articulating surface 914 of the work piece, or tibial tray 792. A vessel 922 is positioned around the work piece, or tibial tray 792, for securing the slurry 912. The slurry 912 is advanced by pump 935 toward the polishing zone 924.

Figure 19:
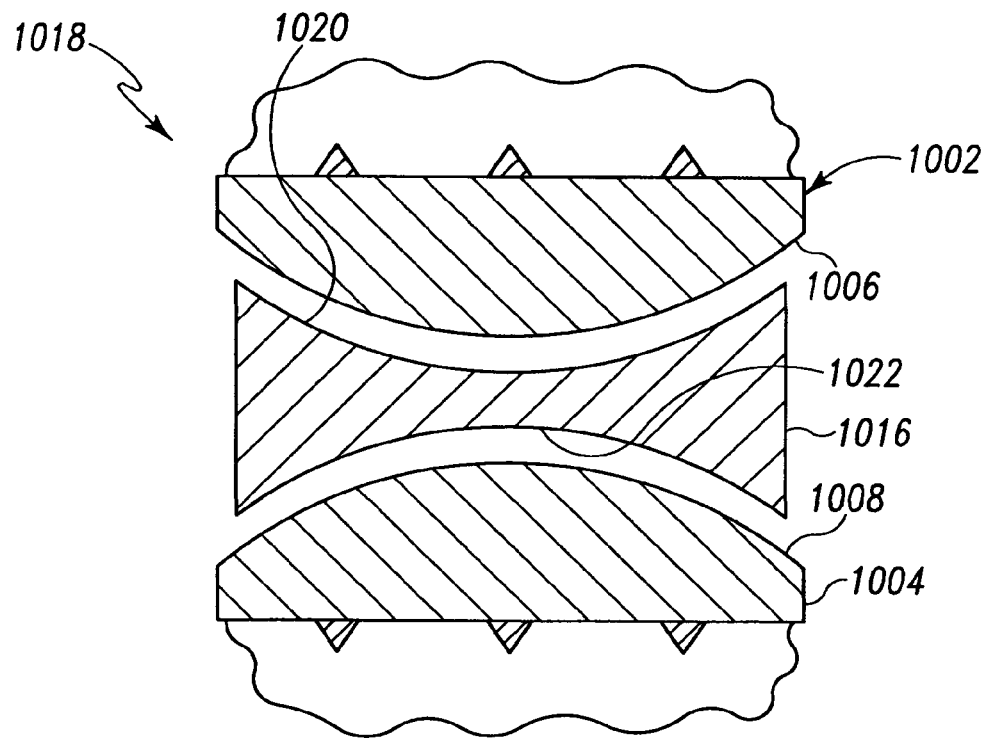
FIG. 19 is a partial plan view partially in cross-section of a vertebral orthopaedic implant for use in performing spine orthopaedic surgery that may be machined in accordance with yet another embodiment of the present invention.
Figure 20:
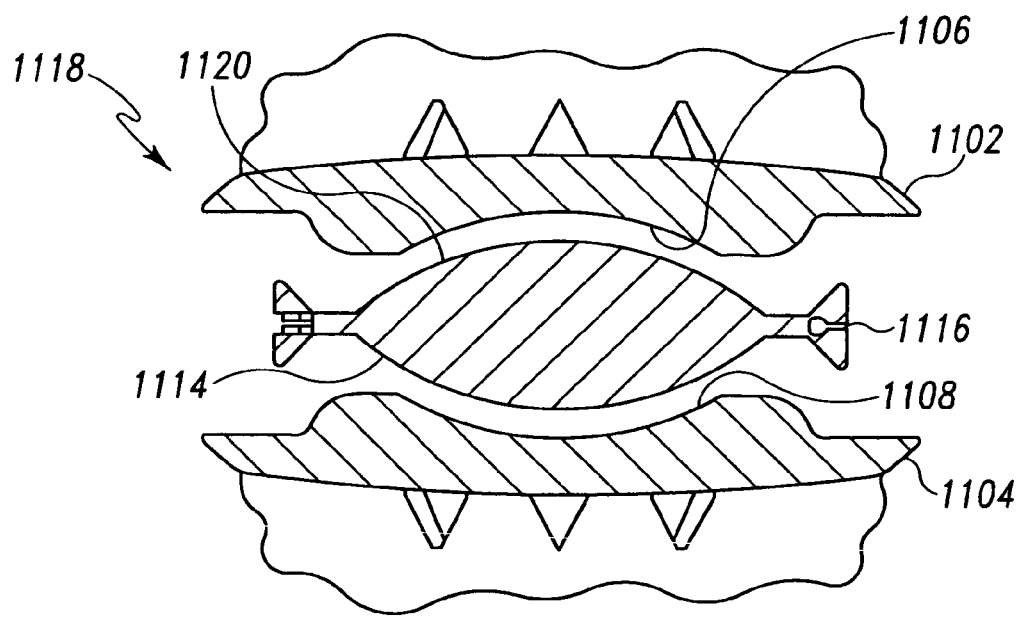
FIG. 20 is a partial plan view partially in cross-section of a Charite'® vertebral orthopaedic implant for use in performing spine orthopaedic surgery that may be machined in accordance with a further embodiment of the present invention.

Referring now to FIGS. 19 and 20, yet another orthopedic component that may be polished with the device of the present invention is shown. Referring now to FIG. 19, a spine prosthesis 1018 is shown. The spine prosthesis 1018 includes a first vertebral component 1002 and a spaced apart second vertebral component 1004. The first vertebral component 1002 includes a convex articulating surface 1006 which may be polished by a device of the present invention. The second vertebral component 1004 includes a convex articulating surface 1008 that may, likewise, be polished by a device according to the present invention. The spine prosthesis 1018 further includes a bearing component 1016 which may be positioned between the first vertebral component 1002 and the second vertebral component 1004. The bearing 1016 may include a first concave articulating surface 1020 as well as a second concave articulating surface 1022 which may be polished by a device according to the present invention.

Referring now to FIG. 20, another orthopedic prosthesis that may be polished with a device according to the present invention is shown. The spine prosthesis 1118 includes a first vertebral component 1102 which includes a concave articulating surface 1106 which may be polished by a device of the present invention. The spine prosthesis 1018 may further include a second vertebral component 1104 which may include a concave articulating surface 1108 which may be polished utilizing a device according to the present invention. The spine prosthesis 1118 may further include a bearing 1116 having opposed convex articulating surfaces 1114 and 1120 which may also be polished by a device of the present invention.

Figure 21:
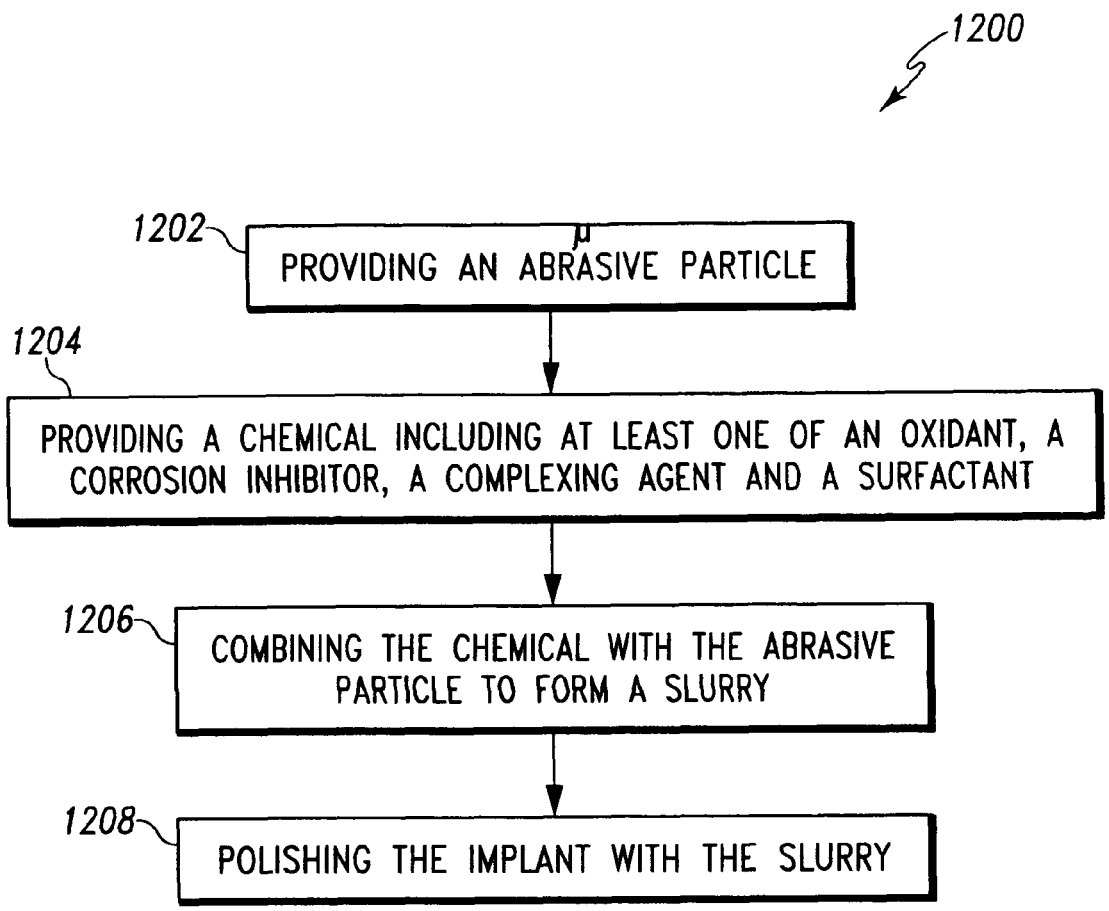
FIG. 21 is a process flow diagram for a yet another method of preparing an articulating surface of a prosthetic component for use in joint arthroplasty surgery according to a further embodiment of the present invention.
Figure 22:
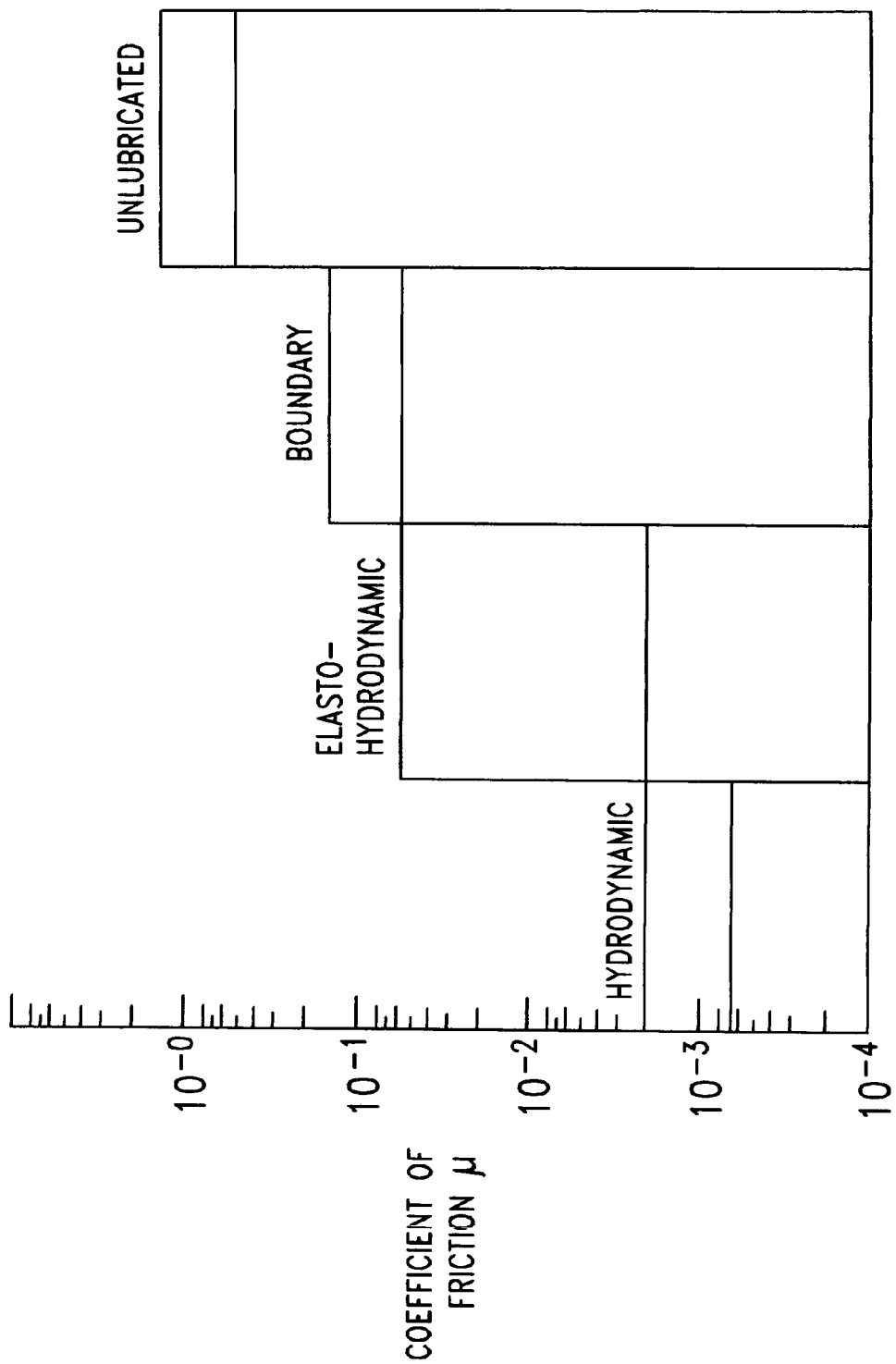
FIG. 22. is a graph of the coefficient of friction for various types of lubrication.
Figure 23:
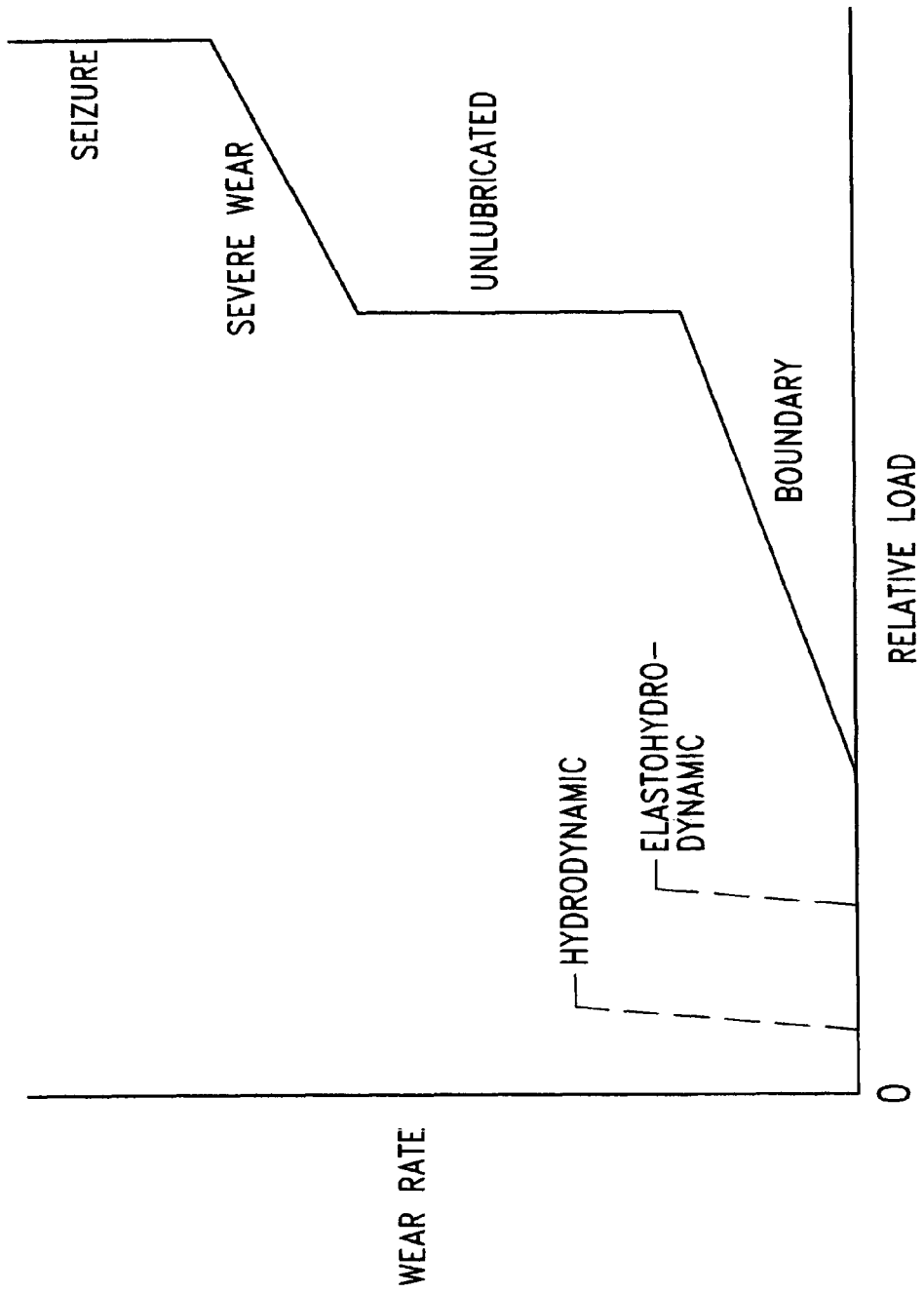
FIG. 23 is a graph of wear rate versus relative load for various types of lubrication.

Referring now to FIG. 21, yet another embodiment of the present invention is shown as method 1200 for reducing the surface roughness of articulating surfaces of orthopedic implants. The method 1200 includes a first step 1202 of providing an abrasive particle. The method includes a second step 1204 of providing a chemical, including at least one of an oxidant, a corrosion inhibitor, a complexing agent, and a surfactant.

The method 1200 may further include a third step 1206 of combining the chemical with the abrasive particle to form a slurry and a fourth step 1208 of polishing the implant with the slurry.

It should be appreciated that the second step 1204 of providing a chemical may include a step of providing a chemical with the oxidant capable of oxidizing one of the metals or phases in the object to be polished to a higher oxidation state than it exists in the bulk alloy.

It should further be appreciated that, the method 1200 of FIG. 21 may include the second step 1204 where the step 1204 provides a chemical comprising a chemical with a corrosion inhibitor capable of preventing corrosion to one phase of the alloy in the presence of slurry components designed to corrode or dissolve other alloy constituents.

It should further be appreciated that, the method 1200 of FIG. 21 may be configured such that the second step 1204, of providing a chemical, may be in the form of a step of providing a chemical with a complexing agent capable of sequestering components removed from the object to be polished.

The method 1200 of FIG. 21, it should be appreciated, may include a form of the second step 1204, of providing the chemical, in the form of a step of providing a chemical with a surfactant capable of lowering the surface tension between the slurry abrasive component and the slurry liquid component, or lowering the surface tension between the object to be polished and the slurry liquid component.

The method 1200 of FIG. 21 may be configured such that the first step 1202, of providing an abrasive particle, may be in the form of providing an abrasive particle which is a metal oxide. It should be further appreciated that, the method 1200 of FIG. 21 may be provided such that the first step 1202, of providing an abrasive particle, may be in the form of providing a metal oxide which includes silicone dioxide.

The method 1200 of FIG. 21 may be such that the fourth step 1208, of polishing the implant with a slurry, includes the step of providing a pad and applying the slurry to the pad. The method 1200 of FIG. 21 may further, it should be appreciated, include the fourth step 1208, of polishing the implant, in the form of polishing the implant with the slurry comprising the step of articulating the implant with respect to the pad while polishing the implant.

The method 1200 may include the fourth step 1208 in the form of a step of polishing the implant with the slurry by applying a force on the implant and/or against the pad. It should be appreciated that an opposite resisting force will occur to react to the applied force. The slurry is positioned between the implant and the pad.

The method 1200 of FIG. 21 may include the additional step of providing a pad including a polyurethane pad.

Although the present invention and its advantages have been described in detail, it should be understood that various changes, substitutions, and alterations can be made therein without departing from the spirit and scope of the present invention as defined by the appended claims.

I claim:

1. A method of reducing the surface roughness of an articulating surface of an orthopaedic implant, said implant comprising of a carbide phase portion and a matrix phase portion, said method comprising:
   providing an abrasive particle;
   providing a chemical including at least one of an oxidant, a corrosion inhibitor, a complexing agent and a surfactant;
   combining the chemical with the abrasive particle to form a liquid slurry; and
   polishing an arcuate portion of the implant with the slurry to;
   (i) etch the carbide phase portion of the arcuate portion with the slurry, and
   (ii) mechanically remove the matrix phase portion from the arcuate portion with the slurry, wherein the etching step of removing the carbide phase portion is processed at a rate equal to or greater than the mechanical rate of removing the matrix phase portion.

2. The method of claim 1, wherein providing a chemical comprises providing a chemical capable of oxidizing a portion of the implant to a higher oxidation state.

3. The method of claim 1, wherein providing a chemical comprises providing a chemical capable of preventing corrosion of one phase of an alloy in the presence of slurry components designed to corrode or dissolve other constituents of the alloy.

4. The method of claim 1, wherein providing a chemical comprises providing a chemical capable of sequestering components removed from the implant.

5. The method of claim 1, wherein providing a chemical comprises providing a chemical with the surfactant capable of lowering a surface tension between a slurry abrasive component and a slurry liquid component.

6. The method of claim 1, wherein providing an abrasive particle comprises providing a metal oxide.

7. The method of claim 6, wherein providing a metal oxide comprises providing silicon dioxide.

8. The method of claim 1, wherein polishing an arcuate portion of the implant with the slurry comprises articulating the implant with a pad.

9. The method of claim 8, wherein polishing an arcuate portion of the implant with the slurry comprises articulating the implant with a pad that is attached to an inflatable support.

10. The method of claim 1, wherein polishing an arcuate portion of the implant with the slurry comprises:
    reducing the surface roughness ($R_a$) of the arcuate portion of the implant to less than 10 nanometers.

11. A method of polishing an articulating surface of an orthopaedic implant, said implant comprising of a carbide phase portion and a matrix phase portion, said method comprising:
    contacting the carbide phase portion of a generally arcuate articulating surface of an implant with a liquid slurry;
    removing the carbide phase portion of the generally arcuate articulating surface using the liquid slurry;
    contacting the matrix phase portion of the generally arcuate articulating surface of the implant with the liquid slurry; and
    mechanically removing the matrix phase portion from the generally arcuate articulating surface with the liquid slurry, wherein the step of removing the carbide phase portion is processed at a rate equal to or greater than the rate of mechanically removing the matrix phase portion.

12. The method of claim 11, further comprising:
    providing a corrosion inhibitor in the slurry to inhibit corrosion of the matrix phase portion by the slurry.

13. The method of claim 12, further comprising:
    providing a complexing agent to sequester the removed matrix phase portion.

14. The method of claim 11, further comprising:
    providing an abrasive particle;
    providing a chemical including at least one of an oxidant, a corrosion inhibitor, a complexing agent and a surfactant; and
    combining the chemical with the abrasive particle to form the slurry.

15. The method of 14, wherein providing a chemical comprises providing a chemical capable of oxidizing a material in the implant to a higher oxidation state.

16. The method of claim 14, wherein providing a chemical comprises providing a chemical capable of preventing corrosion of one phase of an alloy in the presence of slurry components designed to corrode or dissolve other constituents of the alloy.

17. The method of claim 14, wherein providing a chemical comprises providing a chemical with a surfactant capable of lowering a surface tension between a slurry abrasive component and a slurry liquid component.

18. The method of claim 14, wherein providing a chemical comprises providing a chemical with a surfactant capable of lowering a surface tension between the implant and a slurry liquid component.

19. The method of claim 11, wherein mechanically removing a matrix phase portion comprises articulating the implant with a pad that is attached to an inflatable support.

20. The method of claim 11, further comprising:
    determining a rate of material removal from the implant with a controller; and
    controlling the removal of material from the implant based upon the determined rate of material removal.

* * * * *